US012637703B2

(12) United States Patent
Matoori et al.

(10) Patent No.: US 12,637,703 B2

(45) Date of Patent: May 26, 2026

(54) COMPOSITIONS AND METHODS FOR DETECTION OF OXIDIZABLE ANALYTES

(71) Applicant: President and Fellows of Harvard College, Cambridge, MA (US)

(72) Inventors: Simon Sam Matoori, Cambridge, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1030 days.

(21) Appl. No.: 17/770,146

(22) PCT Filed: Oct. 20, 2020

(86) PCT No.: PCT/US2020/056432

§ 371 (c)(1),
(2) Date: Apr. 19, 2022

(87) PCT Pub. No.: WO2021/080951

PCT Pub. Date: Apr. 29, 2021

(65) Prior Publication Data

US 2022/0403442 A1 Dec. 22, 2022

Related U.S. Application Data

(60) Provisional application No. 62/923,716, filed on Oct. 21, 2019.

(51) Int. Cl.
*C12Q 1/28* (2006.01)
*C12Q 1/61* (2006.01)
(Continued)

(52) U.S. Cl.
CPC ................. *C12Q 1/28* (2013.01); *C12Q 1/61* (2013.01); *C12Q 1/26* (2013.01); *G01N 21/6486* (2013.01); *G01N 33/92* (2013.01)

(58) Field of Classification Search
CPC ... C12Q 1/28; C12Q 1/61; C12Q 1/26; G01N 21/64; G01N 21/6428; G01N 21/6486;
(Continued)

(56) References Cited

U.S. PATENT DOCUMENTS 4,772,561 A 9/1988 Genshaw
5,522,977 A 6/1996 Shieh
(Continued)

FOREIGN PATENT DOCUMENTS

WO 2019/062326 A1 4/2019

OTHER PUBLICATIONS

Virk et al. Artificial Cells, Nanomedicine, and Biotechnology, vol. 41, 2013, pp. 255-258.*
(Continued)

*Primary Examiner* — Maureen Wallenhorst
(74) *Attorney, Agent, or Firm* — McCarter & English, LLP; Maria Laccotripe Zacharakis; Wei Song

(57) ABSTRACT

Described herein are compositions that are suitable for use in analyte sensing in biological samples and in medical diagnostics. The compositions include an oxidase capable of oxidizing the analyte of interest to produce hydrogen peroxide, a peroxidase, and a chemical compound, such as a near-infrared fluorescent compound, that is a substrate for the peroxidase. The oxidase, the peroxidase, and the chemical compound are encapsulated by vesicle that includes a lipid or polymeric bilayer, such as liposome and polymersome. The peroxidase catalyzes the oxidation of the chemical compound by hydrogen peroxide. Methods of analyte sensing in biological samples using these compositions, and methods of preparing the compositions are also described.

15 Claims, 19 Drawing Sheets

(51) Int. Cl.
*G01N 21/64* (2006.01)
*G01N 33/92* (2006.01)
*C12Q 1/26* (2006.01)

(58) Field of Classification Search
CPC ........ G01N 33/49; G01N 33/66; G01N 33/92; Y10T 436/144444; Y10T 436/145555; Y10T 436/148888; Y10T 436/203332; Y10T 436/204165; Y10T 436/206664
USPC ......... 436/63, 71, 95, 96, 99, 131, 132, 135, 436/164, 166, 172; 435/10, 11, 14, 25, 435/28; 422/82.05, 82.08
See application file for complete search history.

(56) References Cited

U.S. PATENT DOCUMENTS

| | | | | |
|---|---|---|---|---|
| 5,736,353 | A | 4/1998 | Weavers et al. | |
| 6,265,179 | B1 * | 7/2001 | Zhou | C12Q 1/26 435/14 |
| 2008/0063898 | A1 | 3/2008 | Lally et al. | |
| 2009/0136935 | A1 | 5/2009 | Petersen | |
| 2010/0143897 | A1 * | 6/2010 | Merkler | C12Q 1/48 435/26 |
| 2011/0207821 | A1 | 8/2011 | Framroze | |
| 2017/0252413 | A1 * | 9/2017 | Esener | A61K 9/5115 |
| 2018/0179233 | A1 | 6/2018 | Gamsey et al. | |
| 2022/0133859 | A1 * | 5/2022 | Yang | A61K 47/64 424/451 |

OTHER PUBLICATIONS

Tang et al. Talanta, vol. 68, Aug. 8, 2005, pp. 876-882.*
Hill et al. Biochimica et Biophysica Acta, vol. 1326, 1997, pp. 37-46.*
Matoori et al. Nano-Micro Small, vol. 16, article No. 2000369, Apr. 24, 2020, pp. 1-9.*
Hosseini et al., Enhancement of the peroxidase-like activity of cerium-doped ferrite nanoparticles for colorimetric detection of H2O2 and glucose. Analytical Methods. 2017;9:3519-3524.
Zhang et al., A novel glucose biosensor constructed by glucose oxidase immobilized with methylene blue intercalated layered lanthanum niobic acid nanocomposite. Materials Letters. Nov. 15, 2014;135:39-42.
International Search Report and Written Opinion for Application No. PCT/US2020/056432, dated Feb. 26, 2021, 12 pages.

* cited by examiner

COMPOSITIONS AND METHODS FOR DETECTION OF OXIDIZABLE ANALYTES

CROSS-REFERENCE TO RELATED APPLICATIONS

The instant application is a 35 U.S.C. § 371 national stage filing of International Application No. PCT/US2020/056432, filed on Oct. 20, 2020, which claims priority to U.S. Provisional Application No. 62/923,716, filed on Oct. 21, 2019. The entire contents of each of the aforementioned applications are incorporated herein by reference.

STATEMENT OF GOVERNMENT SUPPORT

This invention was made with U.S. government support under HL021796 awarded by the National Institutes of Health. The government has certain rights in the invention.

BACKGROUND

In emergency medicine, blood lactate is a surrogate marker for disease severity and treatment response in hypoperfusion-related conditions such as sepsis, trauma, and cardiac arrest. Hypoperfusion-associated hyperlactatemia (i.e., increased blood lactate levels) stems from lactate-producing anaerobic glycolysis, which is a characteristic metabolic process in hypoxic tissues.

Blood glucose levels of about 7 mM (hyperglycemia) are a hallmark of diabetes mellitus, a highly prevalent metabolic disease. A tight control of blood glucose levels with glucose-lowering drugs has been shown to decrease the risk of diabetes-related complications (e.g., retinopathy, neuropathy, kidney failure) such that patients are advised to measure their blood glucose levels frequently. Moreover, hyperglycemic episodes such as diabetic ketoacidosis (DKA) and hyperosmolar hyperglycemic state (HHS) require emergency medical intervention, since they can lead to coma, and even death, if left untreated.

Hyperuricemia (i.e., serum uric acid level ≥6.8 mg/dL, 0.4 mM) is a highly common condition affecting over 20% of the population in the United States. It is a major risk factor for crystalline monosodium uric acid deposition which clinically manifests as gout, a form of inflammatory arthritis with a prevalence of 3.9% in the United States. Serum uric acid levels are measured and monitored regularly for diagnosing gout and assessing treatment response.

The determination of blood ethanol is of interest in both an out- and in-patient setting as it impairs the fitness to drive and is associated with serious complications, such as confusion, stupor, and coma, when ingested in high amounts. From 2000 to 2015, over 35% of adult motor vehicle crash fatalities in the United States were alcohol-related. In emergency rooms, acute alcohol-related visits are a frequent and serious occurrence, whose rate has increased by about 40% between 2006 and 2014. Moreover, ethanol may be applied as a therapeutic agent, such as in ethylene glycol poisoning.

Methanol poisoning is often related to the ingestion of methanol-containing solutions (e.g., windshield washer fluid, perfumes) and manifests with nausea, vomiting, and ocular symptoms that can lead to blindness. Therefore, the determination of blood methanol levels is of clinical interest for the diagnosis of methanol poisoning.

Most of the current blood analyte biosensing procedures, including lactate, glucose, uric acid, ethanol, and methanol, rely on laboratory electrochemical analyzers, which results in a delay of several hours to days between triage and the blood analyte results. In particular, whole blood samples are often not viable for current biosensing procedures and therefore must be processed beforehand to generate serum or plasma samples, to enable analysis with UV-VIS absorbance- or fluorescence-based methods. The electrochemical point-of-care lactate analyzer Lactate Pro (Arkray, Kyoto, Japan) is currently not indicated for use in intensive care patients, probably due to its susceptibility to changes in hematocrit and partial oxygen pressure as stated in the operating manual. In addition, strip-based handheld lactate analyzers have been associated with biased results (Bonaventura et al., 2015, *J. Sports Sci. Med.,* 14, 203-214; Tanner et al. 2010, *Eur. J. Appl. Physiol.,* 109, 551-559; Gaieski et al., 2013, *West. J. Emerg. Med.,* 14, 58-62; Karon et al., 2007, *Am. J. Clin. Pathol.,* 128, 168-171).

Accordingly, a need remains for strategies for accelerated, point-of-care detection of important metabolites, drugs, and toxic substances in blood.

SUMMARY

Disclosed herein are liposomal compositions that are suitable for the sensing of oxidizable analytes (metabolites, drugs, and toxic substances) in biological samples and their use in medical diagnostics. The liposomal compositions of the invention include a first enzyme which is an oxidase that is capable of oxidizing an analyte of interest to produce hydrogen peroxide. The liposomal compositions also include a second enzyme which is a peroxidase and a chemical compound that is a substrate for the peroxidase. The substrate emits a detectable signal upon conversion by the peroxidase in the presence of hydrogen peroxide as the oxidizing agent. The encapsulation of the assay components in the liposomal core offers the significant advantage in that it provides a separate reaction compartment for the enzymatic reaction to occur which prevents oxidase-generated hydrogen peroxide from being rapidly detoxified by the highly efficient catalase- and glutathione peroxidase-based systems in erythrocytes. Furthermore, the liposomal compositions of the invention promises to enable point-of-care or bedside diagnostic testing of patients. In some embodiments, a whole blood sample may be directly used in the assay without having to separate cell components from the plasma.

In a first aspect, the present disclosure is directed to a composition that includes an oxidase; a peroxidase; a chemical compound that is a substrate for the peroxidase; and a vesicle comprising a lipid or polymeric bilayer. The vesicle encapsulates the oxidase, the peroxidase, and the chemical compound.

In certain embodiments, the chemical compound is selected from the group consisting of a fluorophore, a chromophore, and a luminophore; and wherein upon being acted on by the peroxidase, the chemical compound emits a detectable signal. In one embodiment, wherein upon being acted on by the peroxidase, the peroxidase changes the spectroscopic properties of the chemical compound. In one embodiment, wherein upon being acted on by the peroxidase, the chemical compound emits a detectable signal that is the result of a loss of fluorescence or luminescence. In one embodiment, wherein upon being acted on by the peroxidase, the chemical compound emits a detectable signal that is detectable in whole blood. In one embodiment, wherein upon being acted on by the peroxidase, the chemical compound emits a detectable fluorescence signal that is detectable in the near-infrared (NIR) wavelength region.

In some embodiments, the chemical compound is a fluorophore selected from the group consisting of a fluorescent protein, a xanthene derivative, a cyanine derivative, a polymethine derivative, a squaraine rotaxane derivative, a naphthalene derivative, a coumarin derivative, an oxadiazole derivative, an anthracene derivative, a pyrene derivative, an oxazine derivative, an acridine derivative, an arylmethine derivative, and a tetrapyrrole derivative. In one embodiment, the chemical compound is a sulfonated cyanine derivative. In one embodiment, the chemical compound is a hydrophilic compound. In one embodiment, the cyanine derivative is selected from the group consisting of the compounds represented by the following structural formulas:

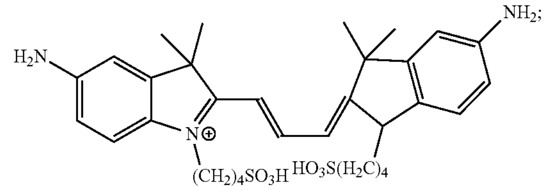

(5-amino-2-((E)-3-((E)-5-amino-3,3-dimethyl-1-(4-sulfobutyl)indolin-2-ylidene)prop-1-en-1-yl)-3,3-dimethyl-1-(4-sulfobutyl)-3H-indol-1-ium)

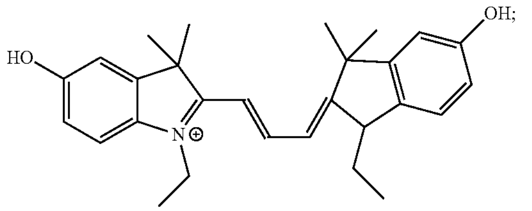

(1-ethyl-2-((E)-3-((E)-1-ethyl-5-hydroxy-3,3-dimethylindolin-2-ylidene)prop-1-en-1-yl)-5-hydroxy-3,3-dimethyl-3H-indol-1-ium)

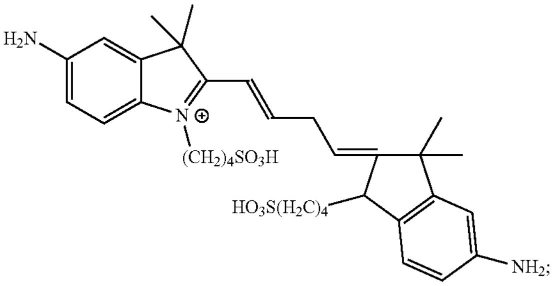

(5-amino-2-((E)-4-((E)-5-amino-1-(4-(mercaptotrioxidaneyl) butyl)-3,3-dimethylindolin-2-ylidene)but-1-en-1-yl)-3,3-dimethyl-1-(4-sulfobutyl)-3H-indol-1-ium

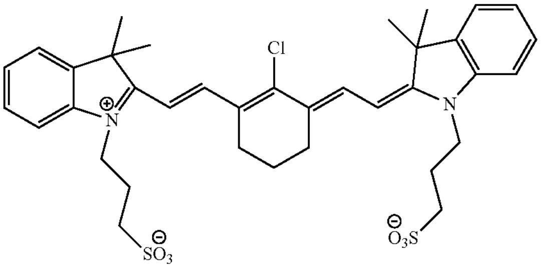

;

(tricarbochlorocyanine Cy•7•Cl)

-continued

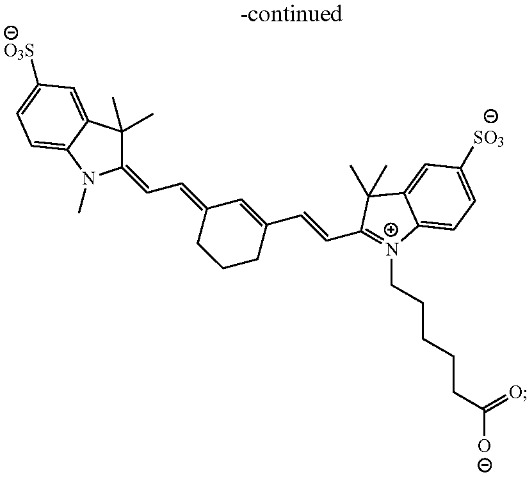

and (sulfo-cyanine 7)

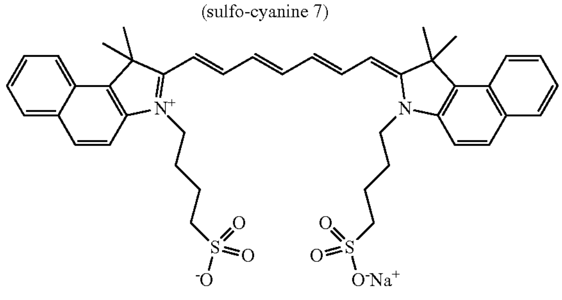

.

(indocyanine green) (ICG)

In one embodiment, the chemical compound is represented by the following structural formula:

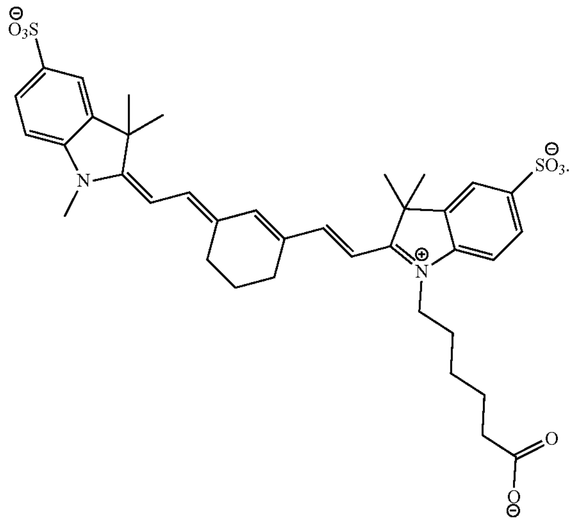

(sulfo-cyanine 7)

In one embodiment, the chemical compound is a chromophore selected from the group consisting of cardiogreen (indocyanine green), methylene blue, and riboflavin.

In one embodiment, the chemical compound is a luminophore selected from the group consisting of lanthanum, cerium, praseodymium, neodymium, promethium, samarium, europium, gadolinium, terbium, dysprosium, holmium, thulium, ytterbium, and lutetium.

In certain embodiments, the chemical compound is present in the composition at a concentration of about 50 μM to about 500 μM. In one embodiment, the chemical compound is present in the composition at a concentration of about 100 μM to about 200 μM.

In some embodiments, the oxidase is capable of oxidizing an analyte to yield hydrogen peroxide. In one embodiment, the oxidase is selected from the group consisting of lactate oxidase, glucose oxidase, alcohol oxidase, urate oxidase, cholesterol oxidase, and bilirubin oxidase. In one embodiment, the oxidase is present in the composition at a concentration of about 2 U/mL to about 20 U/mL, e.g., about 2 U/mL to about 10 U/mL, about 5 U/mL to about 10 U/mL, about 10 U/mL to about 15 U/mL, about 10 U/mL to about 20 U/mL. In one embodiment, the oxidase is present in the composition at a concentration of about 5 U/mL to about 18 U/mL.

In certain embodiments, the peroxidase is horseradish peroxidase. In one embodiment, the peroxidase is present in the composition at a concentration of about 0.1 U/mL to about 1.0 U/mL. In one embodiment, the peroxidase is present in the composition at a concentration of about 0.4 U/mL to about 0.6 U/mL.

In some embodiments, the vesicle has a level of permeability that allows uptake of an analyte from a biological sample into the vesicle. In one embodiment, the biological sample is a whole blood sample. In one embodiment, the vesicle has a level of permeability that further does not allow release of the chemical compound out of the vesicle. In one embodiment, the vesicle serves as a physical barrier to hydrogen peroxide generated by the oxidase such that the peroxidase acts on the hydrogen peroxide before the hydrogen peroxide can be released out of the vesicle.

In some embodiments, the vesicle is present in the composition at a phospholipid concentration of about 1.0 mM to about 10.0 mM. In one embodiment, the vesicle is present in the composition at a phospholipid concentration of about 1.0 mM to about 5.0 mM. In one embodiment, the vesicle is present in the composition at a phospholipid concentration of about 1.0 mM to about 2.5 mM.

In one embodiment, the vesicle includes a lipid bilayer. In one embodiment, the vesicle is a liposome. In another embodiment, the vesicle includes a polymeric bilayer. In one embodiment, the vesicle is a polymersome.

In some embodiments, the lipid bilayer includes a phospholipid. In one embodiment, the phospholipid is a PEGylated phospholipid. In one embodiment, the phospholipid is in the lipid bilayer is a phospholipid having a gel-to-liquid phase transition temperature of 35° C. or higher. In one embodiment, the phospholipid is selected from the group consisting of egg sphingomyelin, 1,2-dipalmitoyl-sn-glycero-3-phosphocholine (DPPC), 1,2-distearoyl-sn-glycero-3-phosphocholine, and 1,2-ditetradecanoyl-sn-glycero-3-phosphoethanolamine, and hydrolyzed soy phosphocholine. In one embodiment, the phospholipid is 1,2-dipalmitoyl-sn-glycero-3-phosphocholine (DPPC). In one embodiment, the phospholipid is 1,2-distearoyl-sn-glycero-3-phosphoethanolamine-N-[carboxy(polyethylene glycol)-2000].

In certain embodiments, the lipid bilayer further includes a non-phosphorylated lipid. In one embodiment, the non-phosphorylated lipid is selected from the group consisting of a fatty acid, a wax, a sterol, a monoglyceride, a diglyceride, and a triglyceride. In one embodiment, the non-phosphorylated lipid is cholesterol.

In a second aspect, the present disclosure is directed to a system for the detection of an analyte in a biological sample, that includes the composition in accordance with the first aspect of the invention and at least a buffer solution. In one embodiment, the system is for point-of-care or bedside detection of the analyte. In one embodiment, the biological sample is a whole blood sample. In one embodiment, the system further includes a detection device selected from the group consisting of a fluorescence detector, a spectrophotometer, a UV-VIS absorbance detector, a chemosensor, and a luminescence detector. In one embodiment, the buffer solution has a pH level that enhances the uptake of the analyte from the biological sample into the vesicle.

In a third aspect, the present disclosure relates to a kit for the detection of an analyte in a biological sample, that includes the composition in accordance with the first aspect of the invention and at least a buffer solution. In one embodiment, the system is for point-of-care or bedside detection of the analyte. In one embodiment, the biological sample is a whole blood sample. In one embodiment, the system further includes a device selected from the group consisting of a fluorescence detector, a spectrophotometer, a UV-VIS absorbance detector, a chemosensor, and a luminescence detector. In one embodiment, the buffer solution has a pH level that accelerates the uptake of the analyte from the biological sample into the vesicle.

In a fourth aspect, the present disclosure relates to a method for diagnosing a medical condition or assessing the efficacy of a treatment regimen of the medical condition in a subject. The method includes contacting a biological sample from the subject with a composition in accordance with the first aspect of the invention; and detecting an analyte in the biological sample by detecting a detectable signal. The presence of the analyte at a pre-determined level is indicative of the medical condition in the subject. In one embodiment, the detectable signal is the result of a loss of fluorescence or luminescence. In one embodiment, the medical condition is selected from the group consisting of hypoperfusion, sepsis, trauma, cardiac arrest, myocardial infarction, stroke, hyperlactatemia, diabetes mellitus, hyperglycemia, diabetic ketoacidosis (DKA), hyperosmolar hyperglycemic state (HHS), alcohol intoxication, methanol poisoning, gout, and hyperuricemia. In one embodiment, the method is for point-of-care or bedside diagnostic testing of the medical condition. In one embodiment, the biological sample is a whole blood sample.

In a fifth aspect, the present disclosure relates to a method for detecting an analyte in a biological sample. The method includes contacting a biological sample with a composition in accordance with the first aspect of the invention; and detecting a detectable signal. The detectable signal is indicative of the presence of the analyte in the biological sample. In one embodiment, the detectable signal is the result of a loss of fluorescence or luminescence. In one embodiment, the analyte is selected from the group consisting of a metabolite, a drug molecule, and a toxic substance. In one embodiment, the analyte is selected from the group consisting of lactate, glucose, ethanol, methanol, uric acid, cholesterol, and bilirubin. In one embodiment, the analyte is a drug molecule. In one embodiment, the method is for point-of-care or bedside detection of the analyte. In one embodiment, the biological sample is a whole blood sample.

In a sixth aspect, the present disclosure relates to a method for preparing a composition in accordance with the first aspect of the invention, wherein the vesicle includes a lipid bilayer. The method includes dissolving phospholipid in an organic solvent to form a phospholipid solution; removing the solvent from the phospholipid solution to form a dried phospholipid film; rehydrating the phospholipid film in an aqueous buffer that includes the oxidase, the peroxidase, and the chemical compound to form a liposomal mixture; and heating the liposomal mixture to form the composition.

In one embodiment, the organic solvent includes chloroform, dichloromethane, methanol, or a mixture thereof.

In some embodiments, the phospholipid is rehydrated at a phospholipid concentration of about 25 mM to about 50 mM. In one embodiment, the phospholipid is rehydrated at a phospholipid concentration of about 30 mM to about 35 mM.

In certain embodiments, the phospholipid solution further includes a non-phosphorylated lipid. In one embodiment, the non-phosphorylated lipid is selected from the group consisting of a fatty acid, a wax, a sterol, a monoglyceride, a diglyceride, and a triglyceride. In one embodiment, the non-phosphorylated lipid is cholesterol. In some embodiments, the phospholipid solution further includes a phospholipid-polymer conjugate. In one embodiment, the phospholipid-polymer conjugate is DSPE-PEO 2000.

In some embodiments, the liposomal mixture is heated at about 40° C. to about 60° C. In one embodiment, the liposomal mixture is heated in the presence of mechanical agitation.

In one embodiment, the solvent from the phospholipid solution is removed using a dry nitrogen or argon stream, or by rotary evaporation.

BRIEF DESCRIPTION OF THE DRAWINGS

FIG. 2A is a graph showing the relative fluorescence intensity of cyanine and sulfo-cyanine near-infrared (NIR) hydrophilic dyes at different hydrogen peroxide concentrations in HRP-containing buffer.

FIG. 2B is a graph showing the relative fluorescence intensity of IRDye® near-infrared (NIR) dyes at different hydrogen peroxide concentrations in HRP-containing buffer.

FIG. 2C is a graph showing the relative fluorescence intensity of S7 and indocyanine green (ICG) dyes at different hydrogen peroxide concentrations in HRP-free and HRP-containing buffers.

FIG. 3B is a graph showing the relative fluorescence intensity of different S7 concentrations at different hydrogen peroxide concentrations in HRP-containing buffer.

FIG. 3C is a graph showing the absorbance spectra of S7 concentrations at different hydrogen peroxide concentrations in HRP-containing buffer.

FIG. 3D is a graph showing the relative fluorescence intensity of different ICG concentrations at different hydrogen peroxide concentrations in HRP-containing buffer.

FIG. 3E is a graph showing the relative fluorescence intensity of several NIR dyes and the superoxide-sensitive dye DHE (positive control) at different concentrations of the superoxide radical source SOTS-1 (E).

FIG. 4A is a graph showing the relative fluorescence intensity of S7- and HRP-containing liposomes at different hydrogen peroxide concentrations in PBS and in hydrogen peroxide-spiked whole blood.

FIG. 4B is a schematic depiction of lactate sensing using LO/HRP/S7-containing liposomes.

FIG. 4C is a graph showing the relative fluorescence intensity of LO/HRP/S7-containing liposomes at different lactate concentrations in PBS.

FIG. 4D is a graph showing the relative fluorescence intensity of LO/HRP/S7-containing liposomes in lactate-spiked whole blood at an outer phase pH of 7.4 for 105 min.

FIG. 4E a graph showing the relative fluorescence intensity of LO/HRP/S7-containing liposomes in lactate-spiked whole blood at an outer phase pH of 6.1 (lowered from pH 7.4 by adding isotonic phosphate buffer 150 mM at pH 5.9 to the solution).

FIGS. 4F and 4G evaluate the outer phase pH dependence of lactate sensing in spiked bovine whole blood. FIG. 4F is a graph showing the relative fluorescence intensity of LO/HRP/S7-containing liposomes in lactate-spiked whole blood at an outer phase pH of 6.1 or 7.4. FIG. 4G is a graph showing the relative fluorescence intensity of LO/HRP/S7-containing liposomes with different S7 concentrations in lactate-spiked whole blood at pH 6.1. Inner phase composition: S7 concentration: 100 μM; HRP concentration: 0.5 U/mL; LO concentration: 5 U/mL; buffer composition of inner phase: isotonic phosphate buffer 50 mM at pH 7.4; buffer composition of outer phase: isotonic phosphate buffer 38 mM at pH 7.4 (FIG. 4F) and isotonic phosphate buffer 90 mM at pH 6.1 (FIG. 4G); whole blood volume fraction: 25% (v/v) (FIG. 4F) and 10% (v/v) (FIG. 4G); incubation at room temperature. LO: lactate oxidase. All results as means±SD (n=3).

FIG. 6A is a graph showing the relative fluorescence intensity of GO/HRP/S7-containing liposomes at different glucose concentrations in PBS. FIG. 6B is a graph showing the relative fluorescence intensity of GO/HRP/S7-containing liposomes in glucose-spiked bovine whole blood. FIG. 6C is a graph showing the relative fluorescence intensity of GO/HRP/S7-containing liposomes in glucose-spiked bovine whole blood at 100 μM or 200 μM S7. S7 concentration: 100 μM or 200 μM; HRP concentration: 0.5 U/mL; GO concentration: 5 U/mL; buffer composition of inner phase: isotonic phosphate buffer 50 mM at pH 7.4; buffer composition of outer phase: isotonic phosphate buffer 38 mM at pH 7.4; whole blood volume fraction: 25% (v/v); incubation at room temperature. GO: glucose oxidase. The analyte concentrations (x-axis) refer to their final concentrations in the assay mixture. All results as means+SD (n=3).

FIG. 7A is a graph showing the relative fluorescence intensity of AO/HRP/S7-containing liposomes at different ethanol concentrations in PBS. FIG. 7B is a graph showing the relative fluorescence intensity of AO/HRP/S7-containing liposomes in non-spiked (control) and ethanol-spiked bovine whole blood. FIG. 7C is a graph showing the relative fluorescence intensity of AO/HRP/S7-containing liposomes in non-spiked (control) and methanol-spiked bovine whole blood. FIG. 7D is a graph showing the relative fluorescence intensity of AO/HRP/S7-containing liposomes in ethanol-spiked bovine whole blood at 10 min. FIG. 7E is a graph showing the relative fluorescence intensity of AO/HRP/S7-containing liposomes in methanol-spiked bovine whole blood. S7 concentration: 100 μM; HRP concentration: 0.5 U/mL; AO concentration: 18 U/mL; buffer composition of inner phase and outer phase: isotonic phosphate buffer 50 mM at pH 7.4; buffer composition of outer phase: isotonic phosphate buffer 38 mM at pH 7.4; whole blood volume fraction: 25% (v/v); 10 min incubation time at room temperature. AO: alcohol oxidase. The analyte concentrations (x-axis) refer to their final concentrations in the assay mixture. All results as means+SD (n=3).

FIG. 8 is a graph showing the relative fluorescence intensity of UO/HRP/S7-containing liposomes at different uric acid concentrations in PBS. S7 concentration: 100 μM; HRP concentration: 0.5 U/mL; urate oxidase concentration: 5 U/mL; buffer composition of inner phase and outer phase: isotonic phosphate buffer 50 mM at pH 7.4; incubation at room temperature. The analyte concentrations (x-axis) refer to their final concentrations in the assay mixture. UO: urate oxidase. All results as means±SD (n=3).

FIG. 9A shows the turbidity (i.e., absorbance at 600 nm) of eluted fractions of a liposome-containing sample. FIG. 9B shows the HRP activity of eluted fractions of an HRP-containing sample after incubation with hydrogen peroxide. FIG. 9C shows the percentage of converted lactate of eluted fractions of a lactate oxidase-containing sample after incubation with lactate. FIG. 9D shows the percentage of converted glucose of eluted fractions of a glucose oxidase-containing sample after incubation with glucose. FIG. 9E shows the percentage of converted ethanol of eluted fractions of an alcohol oxidase-containing sample after incubation with ethanol. FIG. 9F shows the percentage of converted urate of eluted fractions of a urate oxidase-containing sample after incubation with urate. Lipid concentration: 34 mM (FIG. 9A); enzyme concentration 5 U/mL (FIGS. 9C-9F) except for HRP (0.5 U/mL, FIG. 9B); fraction volume: 0.25 mL. All results as means±SD (n=3).

DETAILED DESCRIPTION

Figure 1:
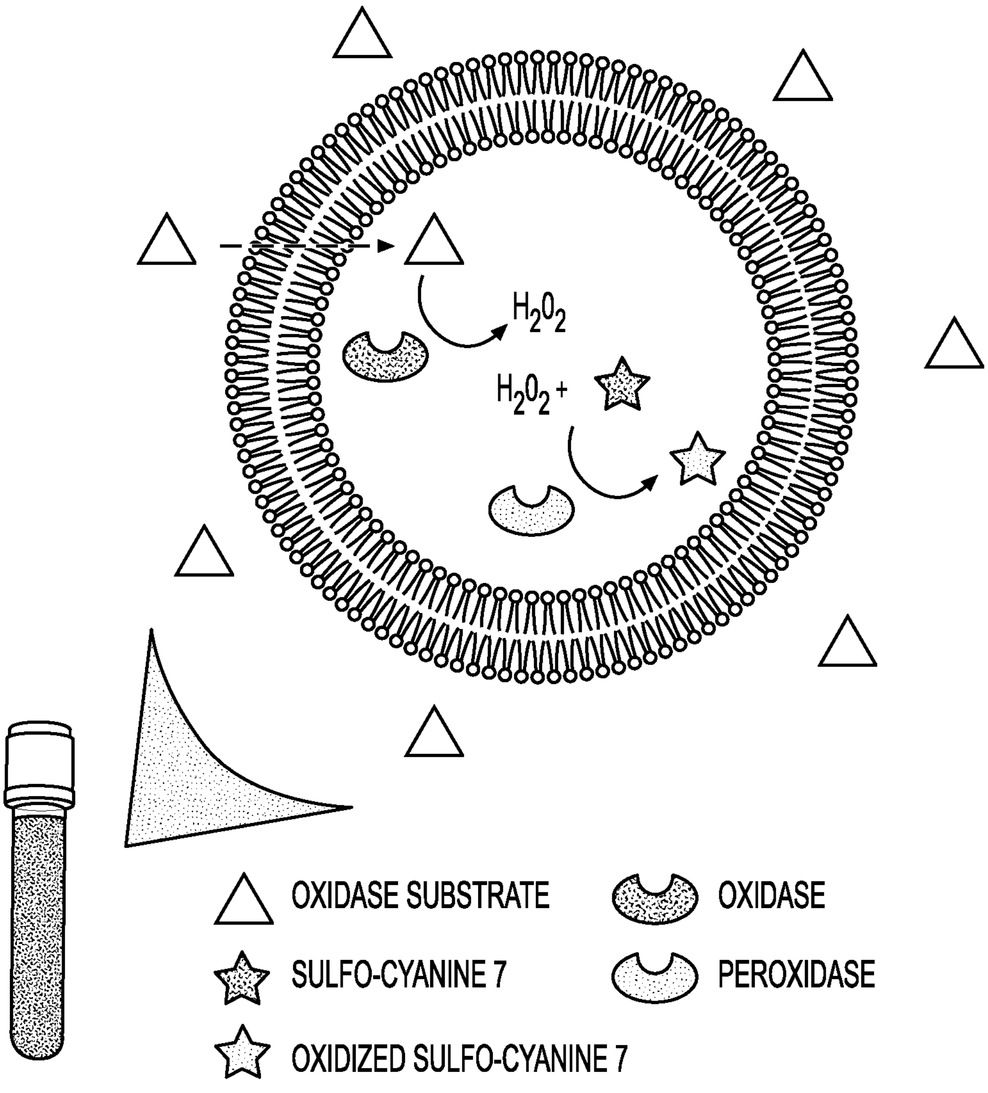
FIG. 1 is a schematic diagram illustrating a composition according an embodiment of the invention: a liposomal composition encapsulating an oxidase, a peroxidase, and a sulfo-cyanine 7 (S7) dye (peroxidase substrate), where the substrate of the oxidase diffuses through the lipid bilayer from the blood into the composition and is converted to hydrogen peroxide by the oxidase. The thus generated hydrogen peroxide is then used by the peroxidase to oxidize the dye which leads to change in spectroscopic properties.

Disclosed herein are liposomal compositions that are suitable for the sensing of oxidizable analytes in biological samples and their use in medical diagnostics. Non-limiting examples of such analytes are metabolites, drug molecules, and toxic substances.

In a first aspect, the present disclosure is directed to a composition that includes an oxidase; a peroxidase; a chemical compound that is a substrate for the peroxidase; and a vesicle comprising a lipid or polymeric bilayer. The vesicle encapsulates the oxidase, the peroxidase, and the chemical compound. In certain embodiments, the chemical compound is selected from the group consisting of a fluorophore, a chromophore, and a luminophore. Upon being acted on by the peroxidase, the chemical compound emits a detectable signal, such as absorbance change that is attributed to changes in the spectroscopic properties of the chemical compound. As used herein, the term "absorbance" refers to a measure of the capacity of a substance to absorb light of a specified wavelength. In one embodiment, the chemical compound emits a detectable signal that is the result of a loss of fluorescence or luminescence. As used herein, the term "luminescence" refers to types of luminescence that are not fluorescence.

In a particular embodiment, upon being acted upon by the peroxidase, the chemical compound emits a detectable signal that is detectable in a biological sample, such as a whole blood sample, a serum sample, a plasma sample, or a sweat sample. For instance, in one embodiment, the chemical compound emits a detectable fluorescence signal that is detectable in the near-infrared (NIR) wavelength region of (i.e., between ~700 nm and ~2500 nM). Near-infrared hydrogen peroxide sensing systems are desirable for whole blood applications due to the interference by hemoglobin.

In a specific embodiment, the detectable signal is the result of a loss of fluorescence.

Non-limiting examples of suitable fluorophores (NIR or otherwise) to include in the compositions of the invention are selected from a fluorescent protein, a xanthene derivative, a cyanine derivative, a polymethine derivative, a squaraine rotaxane derivative, a naphthalene derivative, a coumarin derivative, an oxadiazole derivative, an anthracene derivative, a pyrene derivative, an oxazine derivative, an acridine derivative, an arylmethine derivative, and a tetrapyrrole derivative.

In one embodiment, the fluorophore is a cyanine derivative. In one embodiment, the fluorophore is a sulfonated cyanine derivative. In one embodiment, the cyanine derivative is a hydrophilic compound.

In one embodiment, the fluorophore is represented by the following generic structural formula:

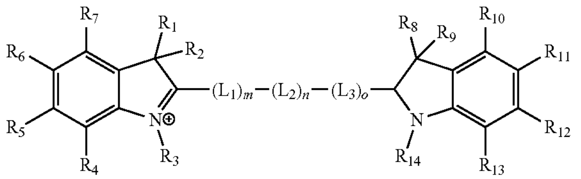

wherein:

$R_1$, $R_2$, $R_3$, $R_4$, $R_5$, $R_6$, and $R_7$ are each and independently selected from hydrogen, $C_{1-4}$ aliphatic, amine (e.g., $NH_2$, NHR, or NRR, wherein R is a $C_{1-4}$ aliphatic group), hydroxyl, $C_{1-4}$ alkoxy, and sulfonate ($SO_3^-$); wherein each $C_{1-4}$ aliphatic group represented by R, $R_1$, $R_2$, $R_3$, $R_4$, $R_5$, $R_6$, and $R_7$ and each $C_{1-4}$ alkoxy represented by $R_1$, $R_2$, $R_3$, $R_4$, $R_5$, $R_6$, and $R_7$ are optionally and independently substituted with sulfonate ($SO_3^-$); and wherein at least one of $R_1$, $R_2$, $R_3$, $R_4$, $R_5$, $R_6$, and $R_7$ is a sulfonate ($SO_3$), or at least one $C_{1-4}$ aliphatic group represented by R, $R_1$, $R_2$, $R_3$, $R_4$, $R_5$, $R_6$, and $R_7$ is optionally and independently substituted with sulfonate ($SO_3^-$); or at least $C_{1-4}$ alkoxy represented by $R_1$, $R_2$, $R_3$, $R_4$, $R_5$, $R_6$, and $R_7$ is optionally and independently substituted with sulfonate ($SO_3^-$);

or alternatively, either $R_4$ and $R_5$, or $R_5$ and $R_6$, or $R_6$ and $R_7$, together with their respective two intervening carbon atoms form an optionally substituted 5- to 6-membered aryl ring (aromatic), an optionally substituted 5- to 6-membered carbocyclyl ring (saturated or semi-saturated or otherwise non-aromatic), an optionally substituted 5- to 6-membered heteroaryl ring (aromatic), or an optionally substituted 5- to 6-membered heterocyclyl ring (saturated or semi-saturated or otherwise non-aromatic);

$R_8$, $R_9$, $R_{10}$, $R_{11}$, $R_{12}$, $R_{13}$, and $R_{14}$ are each and independently selected from hydrogen, $C_{1-4}$ aliphatic, amine (e.g., $NH_2$, NHR', or NR'R', wherein R' is a $C_{1-4}$ aliphatic group), hydroxyl, $C_{1-4}$ alkoxy, and sulfonate ($SO_3^-$); wherein each $C_{1-4}$ aliphatic group represented by R', $R_8$, $R_9$, $R_{10}$, $R_{11}$, $R_{12}$, $R_{13}$, and $R_{14}$ and each $C_{1-4}$ alkoxy represented by $R_8$, $R_9$, $R_{10}$, $R_{11}$, $R_{12}$, $R_{13}$, and $R_{14}$ are optionally and independently substituted with sulfonate ($SO_3^-$); and wherein at least one of $R_8$, $R_9$, $R_{10}$, $R_{11}$, $R_{12}$, $R_{13}$, and $R_{14}$ is a sulfonate ($SO_3$), or at least one $C_{1-4}$ aliphatic group represented by R', $R_8$, $R_9$, $R_{10}$, $R_{11}$, $R_{12}$, $R_{13}$, and $R_{14}$ is optionally and independently substituted with sulfonate ($SO_3^-$); or at least $C_{1-4}$ alkoxy represented by $R_8$, $R_9$, $R_{10}$, $R_{11}$, $R_{12}$, $R_{13}$, and $R_{14}$ is optionally and independently substituted with sulfonate ($SO_3^-$);

or alternatively, either $R_{10}$ and $R_{11}$, or $R_{11}$ and $R_{12}$, or $R_{12}$ and $R_{13}$, together with their respective two intervening carbon atoms form an optionally substituted 5- to 6-membered aryl ring (aromatic), an optionally substituted 5- to 6-membered carbocyclyl ring (saturated or semi-saturated or otherwise non-aromatic), an optionally substituted 5- to 6-membered heteroaryl ring (aromatic), or an optionally substituted 5- to 6-membered heterocyclyl ring (saturated or semi-saturated or otherwise non-aromatic);

$L_1$, $L_2$, and $L_3$ are each and independently selected from $C_{1-4}$ aliphatic, a 5- to 6-membered aryl ring (aromatic), a 5- to 6-membered carbocyclyl ring (saturated or semi-saturated or otherwise non-aromatic), a 5- to 6-membered heteroaryl ring (aromatic), a 5- to 6-membered heterocyclyl ring (saturated or semi-saturated or otherwise non-aromatic); and m, n, and o are each and independently 0 or 1.

Non-limiting examples of suitable NIR cyanine derivatives are compounds represented by the following structural formulas:

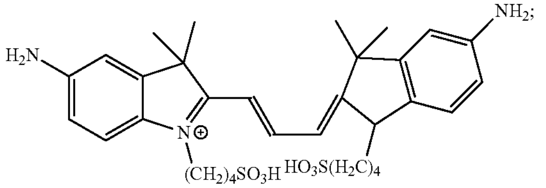

(5-amino-2-((E)-3-((E)-5-amino-3,3-dimethyl-1-(4-sulfobutyl)indolin-2-ylidene)prop-1-en-1-yl)-3,3-dimethyl-1-(4-sulfobutyl)-3H-indol-1-ium)

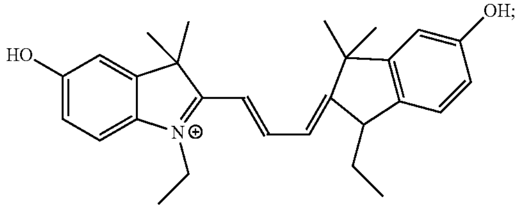

(1-ethyl-2-((E)-3-((E)-1-ethyl-5-hydroxy-3,3-dimethylindolin-2-ylidene)prop-1-en-1-yl)-5-hydroxy-3,3-dimethyl-3H-indol-1-ium)

-continued

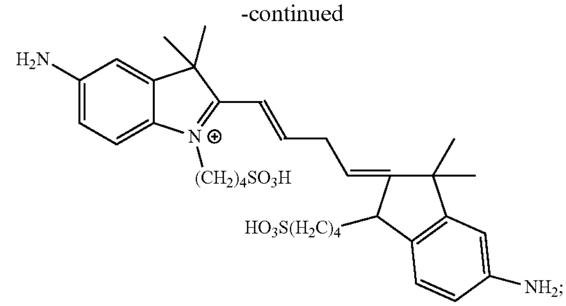

(5-amino-2-((E)-4-((E)-5-amino-1-(4-(mercaptotrioxidaneyl)butyl)-3,3-dimethylindolin-2-ylidene)but-1-en-1-yl)-3,3-dimethyl-1-(4-sulfobutyl)-3H-indol-1-ium

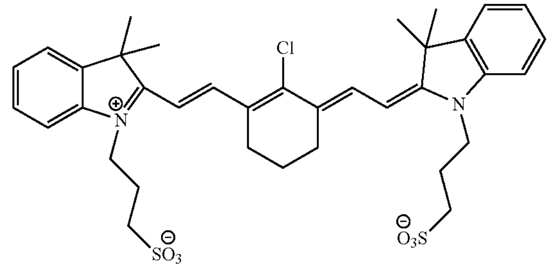

;

(tricarbochlorocyanine Cy•7•Cl)

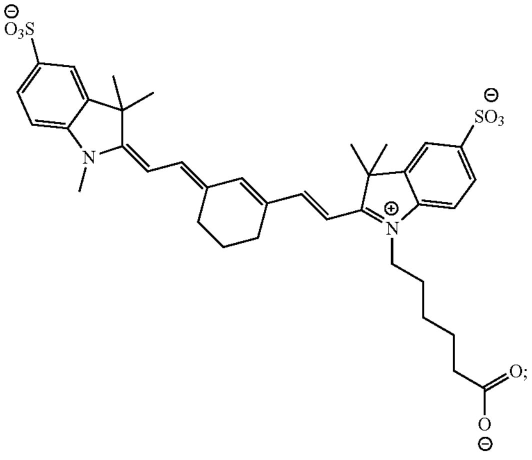

; and (sulfo-cyanine 7)

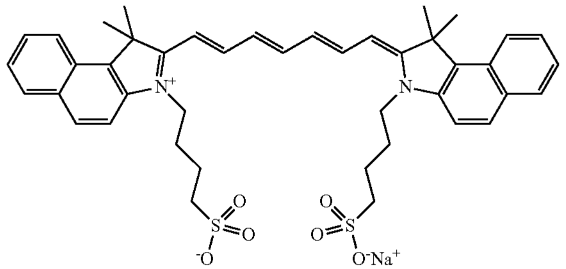

.

(indocyanine green) (ICG)

where suitable counterions of these compounds include trifluoroacetate and a halide (e.g., chloride, bromide, iodide). Further examples of suitable cyanine derivatives are sulfo-cyanine 5, sulfo-cyanine 5.5, sulfo-cyanine 7.5, cyanine 5, cyanine 5.5, cyanine 7, cyanine 7.5, sulfo-cyanine 7 tetrazine, sulfo-cyanine 7 NHS ester, sulfo-cyanine 7 maleimide, sulfo-cyanine 7 dicarboxylic acid, sulfo-cyanine 7 bis-NHS ester, sulfo-cyanine 7 azide, sulfo-cyanine 7 amine, sulfo-cyanine 7 alkyne. In one specific embodiment, the chemical compound in a composition of the invention is represented by the following structural formula:

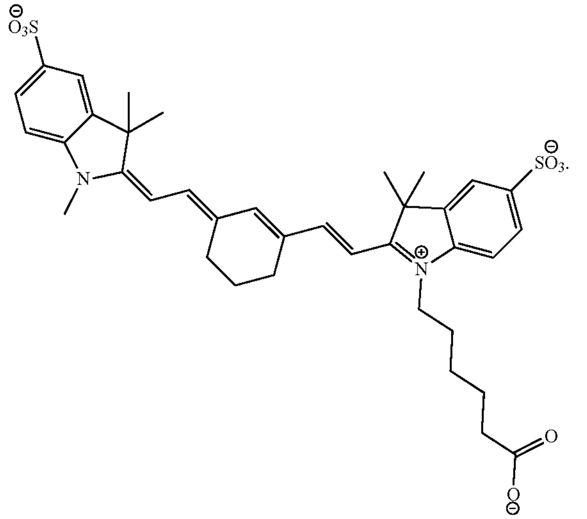

(sulfo-cyanine 7)

Non-limiting examples of suitable NIR chromophores include cardiogreen (indocyanine green), methylene blue, and riboflavin.

Non-limiting examples of suitable NIR luminophores include lanthanum, cerium, praseodymium, neodymium, promethium, samarium, europium, gadolinium, terbium, dysprosium, holmium, thulium, ytterbium, and lutetium.

In some embodiments, the chemical compound is present in the composition at a concentration of about 50 μM to about 500 μM, such as about 50 μM to about 400 μM, about 50 μM to about 300 μM, about 50 μM to about 250 μM, about 50 μM to about 200 μM, about 50 μM to about 100 μM, about 100 μM to about 500 μM, about 100 μM to about 400 μM, about 100 μM to about 300 μM, about 100 μM to about 250 μM, about 100 μM to about 200 μM, about 200 μM to about 250 μM, or about 250 μM to about 300 μM. In one embodiment, the chemical compound is present in the composition at a concentration of about 100 μM to about 200 μM. In one embodiment, the chemical compound is present in the composition at a concentration of about 100 μM. In another embodiment, the chemical compound is present in the composition at a concentration of about 200 μM.

In certain embodiments, the term "oxidase" as used herein refers to an oxidase that is capable of oxidizing an analyte substrate (e.g., a metabolite, a drug molecule, or a toxic substance) to yield hydrogen peroxide. Non-limiting examples of such oxidases include lactate oxidase, glucose oxidase, alcohol oxidase, urate oxidase, cholesterol oxidase, and bilirubin oxidase. In one embodiment, the oxidase in the composition of the invention is lactate oxidase. In one embodiment, the oxidase is glucose oxidase. In one embodiment, the oxidase is alcohol oxidase. In one embodiment, the oxidase is urate oxidase. In one embodiment, the oxidase is cholesterol oxidase. In one embodiment, the oxidase is bilirubin oxidase.

In some embodiments, the oxidase is present in the composition at a concentration of about 2 U/mL to about 20 U/mL, such as about 3 U/mL to about 20 U/mL, about 4 U/mL to about 20 U/mL, about 5 U/mL to about 20 U/mL, about 8 U/mL to about 20 U/mL, about 10 U/mL to about 20

U/mL, about 15 U/mL to about 20 U/mL, about 5 U/mL to about 18 U/mL, about 5 U/mL to about 15 U/mL, or about 5 U/mL to about 10 U/mL. In one embodiment, the oxidase is present in the composition at a concentration of about 5 U/mL to about 18 U/mL In one embodiment, the oxidase is present in the composition at a concentration of about 5 U/mL. In another embodiment, the oxidase is present in the composition at a concentration of about 18 U/mL.

In one embodiment, the peroxidase in the composition of the invention is horseradish peroxidase. In some embodiments, the peroxidase is present in the composition at a concentration of about 0.1 U/mL to about 1.0 U/mL, such as 0.1 U/mL to about 0.8 U/mL, about 0.1 U/mL to about 0.75 U/mL, about 0.2 U/mL to about 1.0 U/mL, about 0.25 U/mL to about 1.0 U/mL, about 0.2 U/mL to about 0.5 U/mL, or about 0.4 U/mL to about 0.6 U/mL. In one embodiment, the peroxidase is present in the composition at a concentration of about 0.4 U/mL to about 0.6 U/mL. In one embodiment, the peroxidase is present in the composition at a concentration of about 0.5 U/mL.

In some embodiments, the concentration levels of the chemical compound, the oxidase and the peroxidase as described above are based on the total volume of a rehydration mixture during preparation of the composition, when the vesicle film such as a phospholipid film is rehydrated with a suitable buffer along with the addition of the enzymes. In other words, in some embodiments, the concentration levels of the chemical compound, the oxidase and the peroxidase described above are based on the total volume of a rehydration mixture during preparation of the composition that comprises the vesicle, the chemical compound, the oxidase, the peroxidase, and a buffer.

The permeability of the vesicle encapsulating the enzymes, the peroxidase substrate and other components is crucial, such that it has a level of permeability that allows uptake of an analyte from a biological sample into the vesicle. In one embodiment, the vesicle serves as a physical barrier to hydrogen peroxide generated by the oxidase such that the peroxidase acts on the hydrogen peroxide before the hydrogen peroxide can be released out of the vesicle. Such permeability allows the assay components of the composition of the invention to be sequestered into the liposome, which in turn enables the peroxidase within the liposome to act primarily on only the hydrogen peroxide that is produced by the oxidation of the analyte within the liposome, and not other hydrogen peroxide found in the biological sample (i.e., allows for high selectivity); prevents, to a considerable degree, the oxidase-generated hydrogen peroxide from being rapidly detoxified by the highly efficient catalase- and glutathione peroxidase-based systems in red blood cells (i.e., allows for high specificity); and enables point-of-care or bedside diagnostic testing of patients, especially a whole blood sample may be directly used in the assay without having to separate cell components from the plasma (i.e., allows for high sensitivity).

To this end, in certain embodiments, the vesicle has a phospholipid concentration of about 1.0 mM to about 10.0 mM, such as about 2.0 mM to about 10.0 mM, about 2.0 mM to about 8.0 mM, about 2.0 mM to about 7.5 mM, about 1.0 mM to about 7.5 mM, about 1.0 mM to about 5.0 mM, about 1.0 mM to about 3.0 mM, about 1.0 mM to about 2.5 mM, about 1.0 mM to about 2.0 mM, or about 1.0 mM to about 1.5 mM. In one embodiment, the vesicle has a phospholipid concentration of about 1.0 mM to about 5.0 mM. In one embodiment, the vesicle has a phospholipid concentration of about 1.0 mM to about 2.5 mM. In one embodiment, the vesicle has a phospholipid concentration of about 1.0 mM to about 2.0 mM. In one embodiment, the vesicle has a phospholipid concentration of about 1.0 mM to about 2.0 mM. In some embodiments, the concentration levels of the vesicle as described above are based on the total volume of an assay mixture.

In one embodiment, the vesicle includes a lipid bilayer. In one embodiment, the vesicle is a liposome. In another embodiment, the vesicle includes a polymeric bilayer. In one embodiment, the vesicle is a polymersome. Non-limiting examples of suitable polymers that may be used in a polymersome include poly(ethylene glycerol) (PEG) and poly(2-methyloxazoline) (forming the hydrophilic blocks); and polydimethylsiloxane (PDMS), poly(caprolactone) (PCL), poly(lactide) (PLA), poly(glycolide) (PLG), poly (lactide-co-glycolide) (PLGA), poly(butadiene) (PBD), poly (styrene) (PS), poly(methyl methacrylate) (PMMA), and physical mixtures thereof (forming the hydrophobic blocks).

In some embodiments, the lipid bilayer in the vesicle includes a phospholipid. Non-limiting examples of suitable phospholipids that may be used in the lipid bilayer of the vesicle include lecithin, lysolecithin, phosphatidylcholine, phosphatidylethanolamine, phosphatidylinositol, phosphatidyl glycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof. In one embodiment, the phospholipid in the lipid bilayer is a PEGylated phospholipid (e.g., PEGylated using phospholipid-polymer conjugates). In one embodiment, the phospholipid in the lipid bilayer is a phospholipid having a gel-to-liquid phase transition temperature of 35° C. or higher. Non-limiting examples of phospholipids having a gel-to-liquid phase transition temperature of 35° C. or higher are egg sphingomyelin, 1,2-dipalmitoyl-sn-glycero-3-phosphocholine (DPPC), 1,2-distearoyl-sn-glycero-3-phosphocholine, 1,2-ditetradecanoyl-sn-glycero-3-phosphoethanolamine, and hydrolyzed soy phosphocholine. In one embodiment the phospholipid is 1,2-dipalmitoyl-sn-glycero-3-phosphocholine (DPPC). In one embodiment, the phospholipid is 1,2-distearoyl-sn-glycero-3-phosphoethanolamine-N-[carboxy(polyethylene glycol)-2000].

In some embodiments, the lipid bilayer in the vesicle further includes a non-phosphorylated lipid. Non-limiting examples of the non-phosphorylated lipid are selected from a fatty acid, a wax, a sterol, a monoglyceride, a diglyceride, and a triglyceride. In one embodiment, the non-phosphorylated lipid is cholesterol.

In a second aspect, the present disclosure is directed to a system for the detection of an analyte in a biological sample, that includes a composition in accordance with the first aspect of the invention including all embodiments thereof and at least a buffer solution. In a third aspect, the present disclosure is directed to a kit (including test kits, assay kits) for the detection of an analyte in a biological sample, that includes a composition in accordance with the first aspect of the invention including all embodiments thereof and at least a buffer solution. Non-limiting examples of suitable buffers include phosphate buffers, Tris buffers, HEPES buffers, IVIES buffers, Bis-Tris buffers, MOPS buffers, each having a pH level of about 6.5 to about 8.5, about 6.0 to about 8.0, about 6.5 to about 8.0, about 6.5 to about 7.5, about 7.0 to about 7.5. In one embodiment, the buffer has a pH level of about 4.0 to about 10.0, about 5.0 to about 9.0, about 6.0 to about 8.5, or about 6.5 to about 8.0. In one embodiment, the biological sample is a whole blood sample. In one embodiment, the system further includes a detection device selected from the group consisting of a fluorescence detector, a spectrophotometer, a UV-VIS absorbance detector, a chemosensor, and a luminescence detector, such as handheld and portable versions of these devices.

In one embodiment, the system is for point-of-care or bedside detection of the analyte. As used herein, the term "point-of-care" or "bedside" refers to medical diagnostic testing at or near the point of care, i.e., at the time and place of patient care. This contrasts with the conventional diagnostic testing that is wholly or mostly confined to the medical laboratory, which entails sending off biological specimens away from the point-of-care and then waiting hours or days to learn the results, during which time care must continue without the desired information. In some embodiments, the system in accordance with the second aspect of the invention allows for measurement of the desired analyte within about 120 minutes or within about 60 minutes, such as within about 30 minutes, within about 25 minutes, within about 20 minutes, within about 15 minutes, within about 10 minutes, within about 8 minutes, within about 6 minutes, within about 5 minutes, within about 3 minutes, within about 2 minutes, within about 1 minute, or within less than 1 minute. In one embodiment, the system in accordance with the second aspect of the invention allows for measurement of the desired analyte within less than 1 minute, such as within about 45 seconds, within about 30 seconds, within about 20 seconds, or within about 1 second. In other words, the system in accordance with the second of the invention reduces the detection and measurement time of an analyte but at least about 10 minutes to about 120 minutes, or about 1 second to about 180 minutes. For example, currently available lactate detection kits yield measurement results in about 3 hours while the system or kit of the present disclosure can provide results within less than about 10 minutes, or within less than about 1 second. In some embodiments, the system in accordance with the second aspect of the invention allows for measurement of the desired analyte at room temperature. In some embodiments, the system in accordance with the second aspect of the invention allows for measurement of the desired analyte between about 15° C. and about 40° C.

In some embodiments, the buffer in the system of the invention has a pH level that enhances the uptake of the analyte from the biological sample into the vesicle. For instance, for lactate detection, it may be desirable to lower the pH level of the assay system from the physiological pH to a slightly acidic pH level of about 6.0 to about 6.5, so as to accelerate the diffusion of lactate molecules across the lipid membrane of the vesicle and to maximize the detection signal.

In a fourth aspect, the present disclosure relates to a method for diagnosing a medical condition or assessing the efficacy of a treatment regimen of the medical condition in a subject. The method includes contacting a biological sample from the subject with a composition in accordance with the first aspect of the invention; and detecting a detectable signal. The presence of the analyte at a pre-determined level is indicative of the medical condition in the subject. For example, the pre-determined level is a threshold level for the analyte (or a range thereof) distinguishing a healthy or untreated subject from a subject suffering from the medical condition and/or receiving the treatment regimen. In one embodiment, the detectable signal is the result of a loss of fluorescence or luminescence. Non-limiting examples of the medical condition diagnosed by the method of the invention are hypoperfusion, sepsis, trauma, cardiac arrest, myocardial infarction, stroke, hyperlactatemia, diabetes mellitus, hyperglycemia, diabetic ketoacidosis (DKA), hyperosmolar hyperglycemic state (HHS), alcohol intoxication, methanol poisoning, gout, and hyperuricemia. In one embodiment, the medical condition diagnosed is hyperlactatemia. In one embodiment, the medical condition diagnosed is hypoperfusion. In one embodiment, the medical condition diagnosed is hyperglycemia. In one embodiment, the medical condition diagnosed is diabetic ketoacidosis (DKA). In one embodiment, the medical condition diagnosed is hyperosmolar hyperglycemic state (HHS). In one embodiment, the medical condition diagnosed is alcohol intoxication. In one embodiment, the medical condition diagnosed is methanol poisoning. In one embodiment, the medical condition diagnosed is hyperuricemia. In one embodiment, the method is for point-of-care or bedside diagnostic testing of the medical condition. In one embodiment, the biological sample is a whole blood sample. Non-limiting examples of a whole blood sample are a venous blood sample and a capillary blood sample. In one embodiment, the biological sample is a plasma sample. In one embodiment, the biological sample is a venous blood sample. In one embodiment, the biological sample is an arterial blood sample. In one embodiment, the biological sample is a capillary blood sample. In one embodiment, the biological sample is a serum sample. In one embodiment, the biological sample is a sweat sample.

In a fifth aspect, the present disclosure relates to a method for detecting an analyte in a biological sample. The method includes contacting a biological sample with a composition in accordance with the first aspect of the invention; and detecting a detectable signal. The detectable signal is indicative of the presence of the analyte in the biological sample. In one embodiment, the detectable signal is the result of a loss of fluorescence or luminescence. In one embodiment, the method further includes obtaining the biological sample from a subject. In one embodiment, the method is for point-of-care or bedside diagnostic testing of the medical condition. In one embodiment, the biological sample is a whole blood sample. In one embodiment, the biological sample is a plasma sample. In one embodiment, the biological sample is a sweat sample. In one embodiment, the analyte is selected from a metabolite, a drug molecule, and a toxic substance. Non-limiting examples of the analyte detected in the method are lactate, glucose, ethanol, methanol, uric acid, cholesterol, and bilirubin. In one embodiment, the analyte is a drug molecule.

In a sixth aspect, the present disclosure relates to a method for preparing the composition in accordance with the first aspect of the invention, wherein the vesicle includes a lipid bilayer. The method includes dissolving phospholipid in an organic solvent to form a phospholipid solution (homogeneous); removing the solvent from the phospholipid solution to form a dried phospholipid film; rehydrating the phospholipid film in an aqueous buffer that includes the oxidase, the peroxidase, and the chemical compound to form a liposomal mixture; and heating the liposomal mixture to form the composition. Non-limiting examples of the organic solvent employed during the initial liposome preparation are chlorinated solvents, diethyl ether, and methanol, or a mixture thereof. In one embodiment, the organic solvent used in the liposome preparation includes chloroform, dichloromethane, methanol, or a mixture thereof.

In some embodiments, the phospholipid is rehydrated at a phospholipid concentration of about 25 mM to about 50 mM in the aqueous buffer including the oxidase, the peroxidase, and the chemical compound to form the liposomal mixture, such as about 30 mM to about 50 mM, about 30 mM to about 40 mM, or about 30 mM to about 35 mM. In one embodiment, the phospholipid is rehydrated at a phospholipid concentration of about 30 mM to about 35 mM. In one embodiment, the phospholipid is rehydrated at a phospholipid concentration of about 35 mM.

In certain embodiments, in the method in accordance with the fifth aspect of the invention, the phospholipid solution further includes a non-phosphorylated lipid. Non-limiting examples of the non-phosphorylated lipid are selected from a fatty acid, a wax, a sterol, a monoglyceride, a diglyceride, and a triglyceride. In one embodiment, the non-phosphorylated lipid is cholesterol.

In certain embodiments, in the method in accordance with the fifth aspect of the invention, the phospholipid solution further includes a phospholipid-polymer conjugate, such as a 1,2-distearoyl-sn-glycero-3-phosphoethanolamine-poly(ethylene glycol) (DSPE-PEG) or a 1,2-distearoyl-sn-glycero-3-phosphoethanolamine-poly(ethylene oxide) (DSPE-PEO), preferably having a molecular weight of about 1000 Da to about 5000 Da, or about 1000 Da to about 4000 Da, about 1000 Da to about 3500 Da, about 1000 Da to about 3000 Da, or about 1000 Da to about 2000 Da. In one embodiment, the phospholipid-polymer conjugate is DSPE-PEO 2000 (i.e., DSPE-PEO having a molecular weight of about 2000 Da).

In certain embodiments, in the method in accordance with the fifth aspect of the invention, the liposomal mixture may be heated at about 40° C. to about 60° C., such as 50° C. to about 60° C., about 45° C. to about 60° C., about 50° C. to about 55° C., about 55° C. to about 60° C., about 56° C. to about 60° C., about 56° C. to about 58° C., or about 55° C. to 56° C. In some embodiments, the liposomal mixture is heated in the presence of mechanical agitation, such as vortexing, or other forms of suitable agitation. In one embodiment, the liposomal mixture is agitated at about 50 rpm to about 250 rpm, about 100 rpm to about 200 rpm.

In certain embodiments, in the method in accordance with the fifth aspect of the invention, the solvent from the phospholipid solution is removed using any conventional method, such as dry nitrogen or argon stream, or by rotary evaporation.

Figure 10:
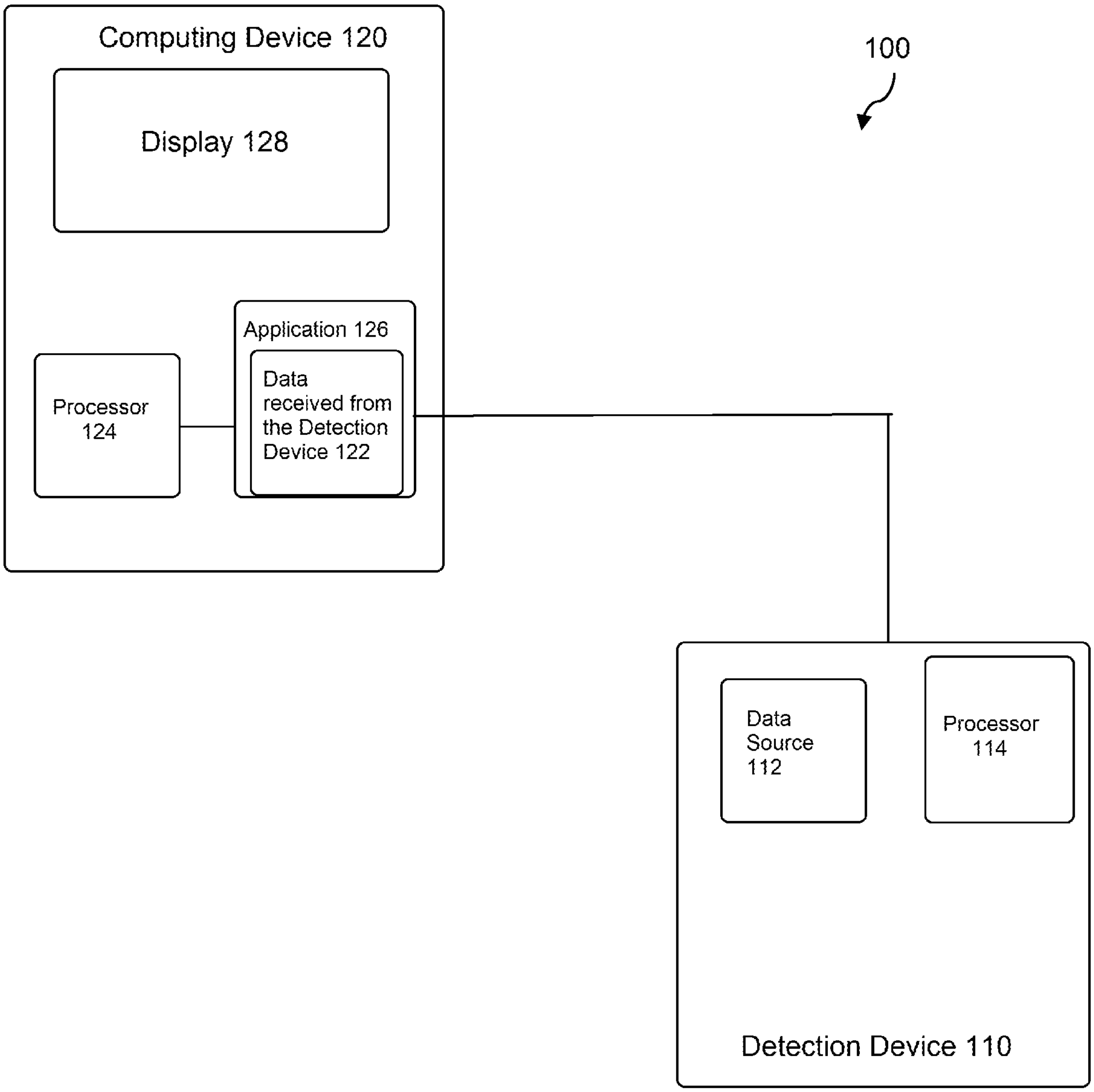
FIG. 10 illustrates a system 100 for the detection and measurement of an analyte, which includes a detection device 110 having a data source 112, and a computing device 120 having a processor 124, an application 126 that is capable of converting a spectroscopic signal to a numerical value for the detected analyte, and a display 128.

The systems described in the present disclosure may incorporate a computing system. Similarly, the methods described in the present may be implemented using a computing system. FIG. 10 provides an embodiment of a system 100 for the detection and measurement of an analyte in a biological sample, that includes a composition in accordance with the first aspect of the invention including all embodiments thereof and at least a buffer solution (not shown in the figure). In one embodiment, the system 100 further includes a detection device 110 and a computing device 120. Non-limiting examples of the detection device are a fluorescence detector, a spectrophotometer, a UV-VIS absorbance detector, a chemosensor, and a luminescence detector, such as handheld and portable versions of these devices. The detection device 110 includes a data source 112, which is the fluorescence or luminescence signal detected in a biological sample, such as a whole blood sample. In some embodiments, the detection device 110 further includes a processor 114 that interprets and generates the fluorescence or luminescence signal data. The detection device 110 is connected to the computing device 120, a processor 124 having an application 126 that is executable on the computing device 120 to process the data received from the detection device 122. The application 126 further converts the fluorescence or luminescence signal data received into a numerical value for the amount of the analyte detected in the biological, which is then communicated to the user at the display 128 (e.g., a liquid-crystal, IPOS, LED, OLED, or AMOLED display). In some embodiments, the computing device 120 is a handheld, mobile computing device such as a smartphone. The computing device 120 can include a network interface configured to interface via one or more network devices with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The computing device 120 may run any operating system, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 100 and performing the operations described herein.

EXAMPLES

Materials and Methods

Screening of NIR Dye Library

NIR dyes were dissolved in water (sulfo-cyanine dyes, Lumiprobe, Hannover, Germany, and all investigated IRDyes except for IRDye 800RS, LI-COR Biosciences, Lincoln, NE) or dimethyl sulfoxide (Sigma Aldrich, St. Louis, MO; cyanine dyes, Lumiprobe, and IRDye 80016, LI-COR Biosciences). 10 μL of dye solution (final 2.5 μM) were added to 100 uL of HRP solution (final 105 mU/mL) and hydrogen peroxide standards (both from Amplex™ Red Hydrogen Peroxide/Peroxidase Assay Kit A22188, Thermo Fisher Scientific, Waltham, MA) in sodium chloride-containing phosphate buffer (Sigma Aldrich) 50 mM at pH 7.5 at 300 mOsmol/kg and protected from light. After 10 min at room temperature, the fluorescence intensity was determined by a plate reader (BioTek NEO2, BioTek, Winooski, VT) at the fluorescence excitation and emission wavelength provided by the manufacturer.

To determine the absorbance spectra of S7, 10 μL of dye solution (final 7.5 μM) were added to 100 μL of HRP solution (final 105 mU/mL) and hydrogen peroxide standards in isotonic phosphate buffer 50 mM at pH 7.5. After 15 min, the absorbance spectra were recorded by a plate reader (BioTek NEO2).

$^1$H NMR Studies of S7

For the NMR experiments, HRP, a stock solution of hydrogen peroxide (30 wt %, Sigma Aldrich), and S7 were diluted in deuterated isotonic sodium chloride-containing phosphate buffer 50 mM at pH 7.5. For the analysis of the reacted S7, S7 (final concentration 1.5 mg/mL), HRP (0.5 U/mL), and hydrogen peroxide (18.75 mM) were incubated for 30 min in deuterated isotonic sodium chloride-containing phosphate buffer 50 mM at pH 7.5. For the analysis of the control S7, S7 (final concentration 0.4 mg/mL) and HRP (0.5 U/mL) were incubated for 30 min in deuterated isotonic sodium chloride-containing phosphate buffer 50 mM at pH 7.5. 1H NMR and 1H-1H homonuclear COSY spectra of native and reacted S7 were recorded using Agilent DD2 600 (Agilent Technologies, Santa Clara, CA).

Superoxide and Hypochloride Testing

Superoxide was generated in accordance with the literature. In brief, SOTS-1 (Cayman Chemicals, Ann Arbor, MI) was dissolved in dimethylformamide (Sigma Aldrich) and added to a near-infrared fluorescent dye-containing (final near-infrared dye concentration 7.5 μM; DHE concentration 10 μM) isotonic phosphate buffer 50 mM at pH 7.5 (final SOTS-1 concentration 62.5 or 125 μM) and protected from light. After 30 min at room temperature, the fluorescence intensity was determined by a plate reader (BioTek NEO2) at the fluorescence excitation and emission wavelength provided by the manufacturer.

To test the effect of hypochlorite on the dyes' fluorescence properties, 10 μL of dye solution (final 2.5 μM) were added to 200 uL of hydrogen peroxide standards in isotonic phosphate buffer 50 mM at pH 7.5 and protected from light. After 10 min at room temperature, the fluorescence intensity was determined by a plate reader (BioTek NEO2) at the fluorescence excitation and emission wavelength provided by the manufacturer.

Encapsulation in Liposomes

For DPPC liposomes, 15.3 μmol DPPC, 18.4 μmol cholesterol, and 0.3 μmol DSPE-PEO(2000) (all from Avanti Polar Lipids, Alabaster, AL), were added as chloroform stock solutions to a glass vial. The organic solvent was subsequently removed by nitrogen flow for at least 1 h and storage in a vacuum desiccator overnight. The dried film was hydrated with 1 mL of dye- and enzyme-containing phosphate buffer 50 mM at pH 7.4 at 300 mOsmol/kg (lipid concentration=34 mM) and immediately treated with three cycles of heating to 56° C. and vortexing for 1.5 min each. After this procedure, the lipid film was not visible anymore.

Purification Procedure

To purify the sample of free enzyme, empty columns (Thermo Scientific Pierce Centrifuge Columns 89897, Thermo Fisher Scientific) were loaded with 6 mL Sepharose CL-6B (Sigma Aldrich) and washed with 18 mL isotonic phosphate buffer 50 mM at pH 7.4. 0.5 mL of sample and 2 mL of isotonic phosphate buffer 50 mM at pH 7.4 were added in steps of 0.25 mL. The fractions of 0.25 mL were collected. Fraction 7 was used for further purification.

MidiTrap G-25 columns (GE Healthcare, Chicago, IL) were used to remove the free S7 and exchange the external phase with isotonic phosphate buffer 150 mM at pH 5.9. Briefly, the column was washed three times with the final buffer, 0.2 mL of the fraction 7 and 0.8 mL of buffer solution were added to the column. The purified enzyme/S7-containing liposomes were eluted with 0.75 mL of buffer and stored at 4° C. protected from light.

The diameter of the liposomes after purification were determined using the Mastersizer3000 laser diffraction particle size analyzer (Malvern Instruments, Malvern, UK). The results are presented as volume distribution (see FIG. 4J and Table 3).

TABLE 3

Diameter (means ± SD, n = 3) of purified liposomes by laser diffraction.

| | D10 (μm) | D50 (μm) | D90 (μm) |
|---|---|---|---|
| Liposomes | 4.5 ± 0.3 | 7.6 ± 0.5 | 12.5 ± 1.1 |

Metabolite Assay in PBS and Whole Blood

To assess the metabolites lactate, glucose, or uric acid in PBS, 50 μL of analyte-containing isotonic phosphate buffer 50 mM at pH 7.4 were incubated with 50 μL of purified liposome solution protected from light at room temperature. The fluorescence intensity was determined by a plate reader (BioTek NEO2) at the fluorescence excitation and emission wavelength of 750 and 773 nm, respectively, in accordance with the manufacturer's instructions. For uric acid, 1 mM was used as the highest concentration due to the low solubility of urate.

For metabolite sensing in whole blood, 50 μL of analyte-containing isotonic phosphate buffer 50 mM at pH 7.4 was added to 50 μL of bovine whole blood (sodium heparin bovine/calf whole blood, Rockland Immunochemicals, Limerick, PA). 50 μL of this mixture was immediately added to 50 μL of purified liposome solution and incubated at room temperature protected from light for 10 min unless stated otherwise. The fluorescence intensity was determined by a plate reader (BioTek NEO2) at the fluorescence excitation and emission wavelength of 750 and 773 nm, respectively, in accordance with the manufacturer's instructions.

Example 1. Screening of a Near-Infrared (NIR) Dye Library and Selection of S7

It has been reported that horseradish peroxidase (HRP), a hydrogen peroxide-consuming enzyme with low substrate selectivity for the oxidized species, was reported to be capable of oxidizing a limited number of fluorescent cyanine-containing structures, of which one was in the near-infrared range. To develop a whole blood hydrogen peroxide assay as part of the metabolite biosensing system, a library of near-infrared cyanine derivatives was screened with the goal of identifying HRP substrates which lose their fluorescence properties in a hydrogen peroxide-dependent manner upon enzymatic oxidation (see FIG. 1).

Figure 2A:
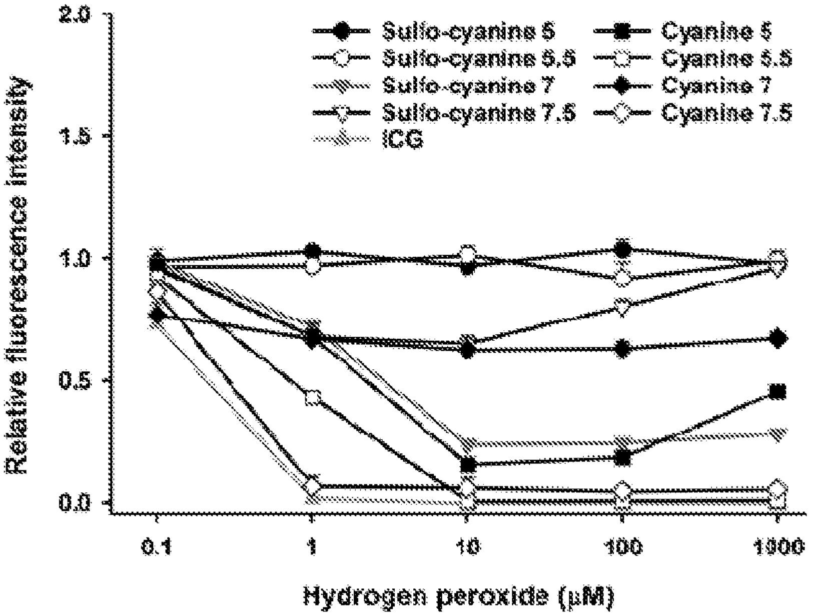
FIGS. 2A-2C are related to screening of near-infrared (NIR) dye library for HRP substrates. NIR dye concentration: 2.5 μM; HRP concentration: 105 mU/mL; buffer composition: phosphate buffer 50 mM at pH 7.5; 10 min incubation time at room temperature. All results as means+SD (n=3).
Figure 2B:
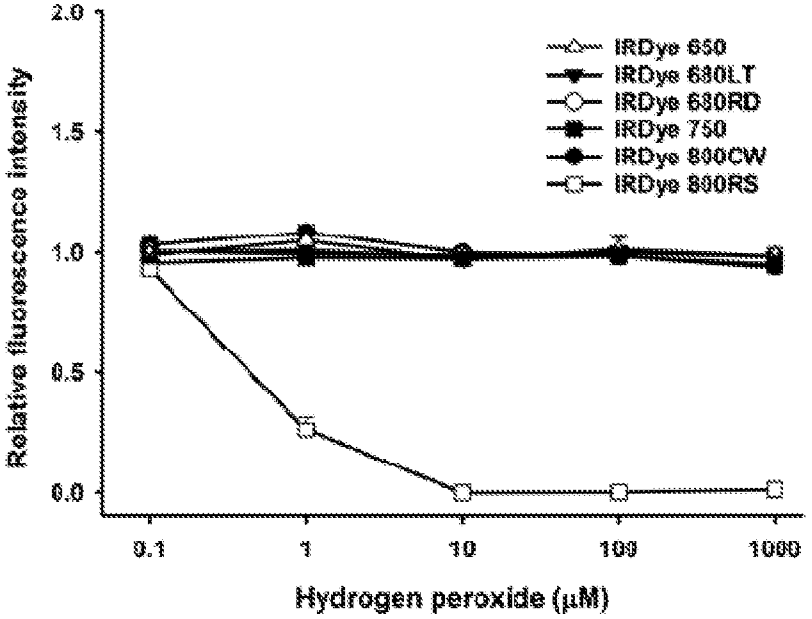
Figure 2C:
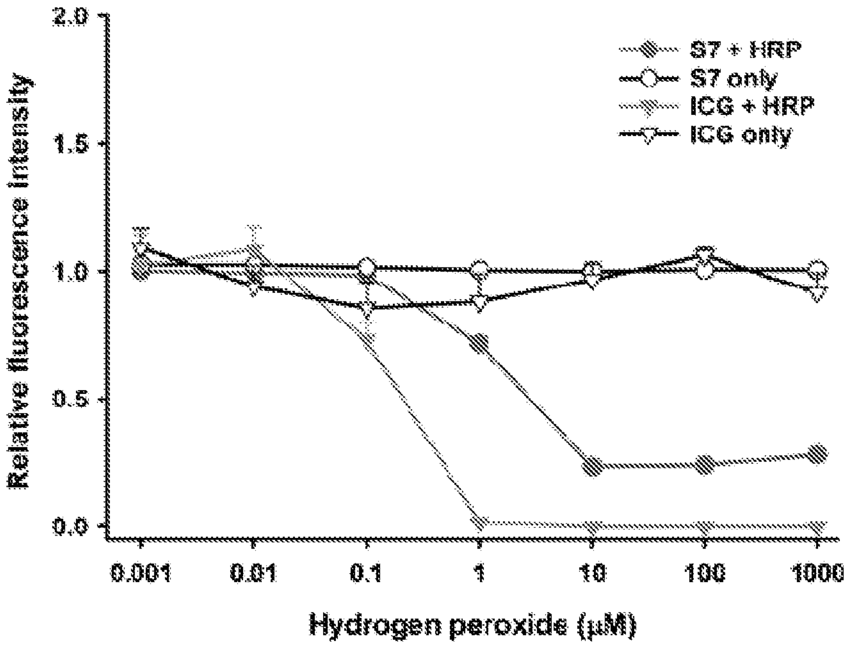
Figure 2D:
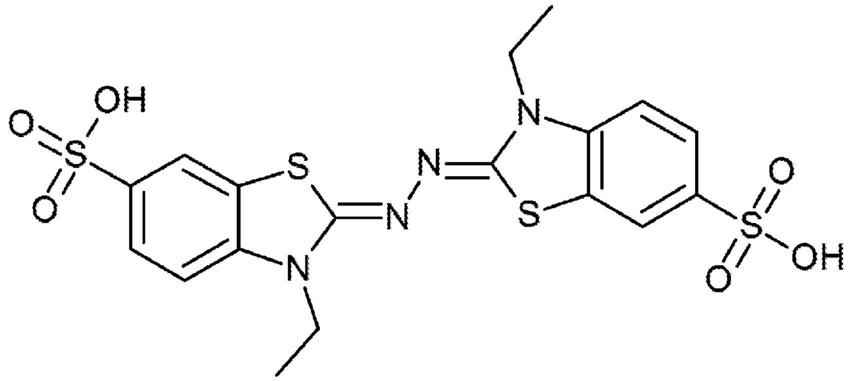
FIG. 2D shows the structure of the known HRP substrate 2,2'-azino-bis(3-ethylbenzothiazoline-6-sulphonic acid) (ABTS).
Figure 2E:
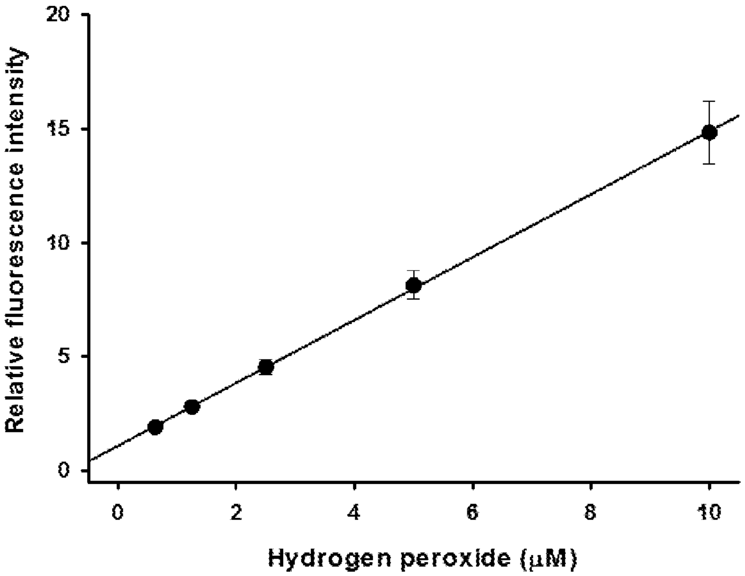
FIG. 2E is a graph showing the relative fluorescence intensity of a homovanillic acid-containing solution in the presence of hydrogen peroxide and HRP, therefore evaluating hydrogen peroxide sensing with homovanillic acid (a known substrate of HRP) and HRP. HRP catalyzes the dimerization of homovanillic acid to a fluorescent product in the presence of hydrogen peroxide. HRP concentration: 0.10 U/mL; homovanillic acid: 0.99 mM; $\lambda_{ex}$ 312 nm; $\lambda_{em}$ 430 nm; incubation time 10 min at room temperature. All results as mean±SD (n=3).
Figure 2F:
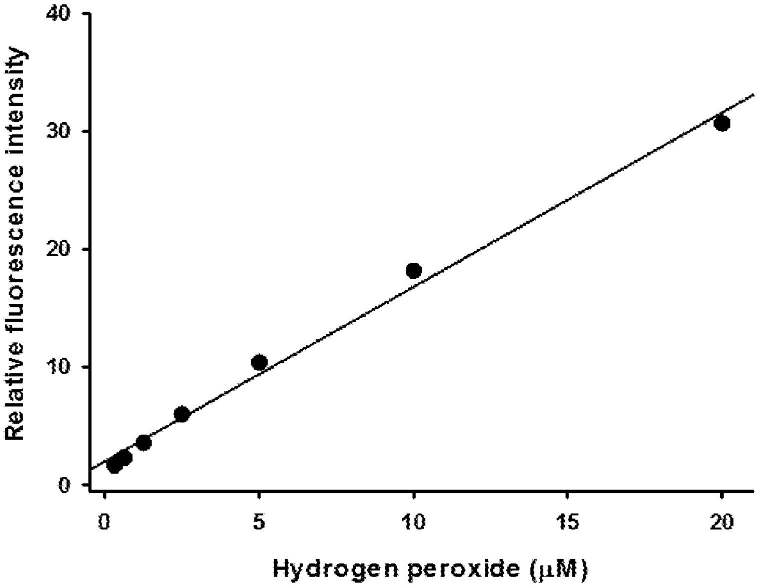
FIG. 2F is a graph showing the relative fluorescence intensity of an Amplex Red®-containing solution in the presence of hydrogen peroxide and HRP, therefore evaluating hydrogen peroxide sensing with Amplex Red® (a known substrate of HRP) and HRP. HRP catalyzes the oxidation of Amplex Red® to the fluorescent product resorufin in the presence of hydrogen peroxide. Excitation/emission wavelengths: $\lambda_{ex}$ 530 nm; $\lambda_{em}$ 590 nm; incubation time 30 min at room temperature. Assay conducted in accordance to manufacturer's instructions. All results as mean±SD (n=3).

Upon exposing a library of commercially available near-infrared fluorescent derivatives to HRP and hydrogen peroxide, a partial to total loss of fluorescence was observed for all hydrophobic and certain hydrophilic cyanine derivatives (see FIGS. 2A and 2B). Among the hydrophilic dyes, only sulfo-cyanine 7 (S7) and indocyanine green (ICG) were oxidized by HRP in a hydrogen peroxide concentration-dependent manner (see FIGS. 2A and 2C). These dyes preserved their fluorescence properties upon exposure to a 400-fold molar excess of hydrogen peroxide in an HRP-free buffer, highlighting the dependence on the enzymatic catalyst (see FIG. 2C). Sulfo-cyanine 7 (S7) was selected as the lead compound due to its high hydrophilicity (clogP 1.8) and fluorescence yield. While this dye was the only substrate of HRP among the molecules with a sulfated indole moiety in the library, S7 is structurally similar to 2,2'-azino-bis(3-ethylbenzothiazoline-6-sulphonic acid) (ABTS), an HRP substrate containing two sulfated benzothiazols (see FIG. 2D). As it was later necessary to encapsulate the hydrogen peroxide sensing system into a liposomal reaction compartment (see FIG. 1), the two negatively charged sulfate groups on the indole moiety likely provide S7 with a high affinity to and a strong retention in the aqueous liposomal core similarly to the sulfated pyrene derivative pyrazine. In contrast, the higher hydrophobicity of ICG (clogP—3.4) and its affinity for hydrophobic liposomal membranes rendered this dye less suitable for the purposes of the present disclosure. Analogous consideration limit the usefulness of the structurally similar near-infrared fluorescent cyanine-based tricarchlorobocyanine which was reported to react with HRP in the presence of hydrogen peroxide in the literature. As the fluorescence properties of ICG are furthermore strongly influenced by solubility-enhancing molecules and proteins (e.g., albumin, amphiphiles), small amounts of free dye (e.g., due to liposomal leakage) may considerably affect the measured fluorescence intensity in whole blood.

Several hydrophobic cyanine derivatives were also oxidized by HRP. Due to their rather low water solubility, these dyes necessitate the addition of organic solvent such as dimethyl sulfoxide for complete dissolution. The impaired stability of liposomes in the presence of organic solvents and the risk of dye partitioning into the hydrophobic liposomal membrane limit the suitability of these dyes for our purposes. As a positive control for the library screening, two known substrates homovanillic acid and Amplex Red® of HRP were enzymatically oxidized in a hydrogen peroxide-dependent manner.

Example 2. S7- and ICG-Mediated Hydrogen Peroxide Sensing

Figure 3A:
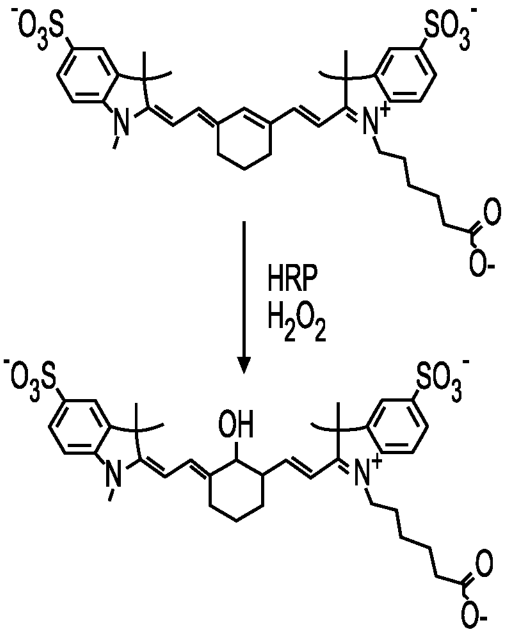
FIG. 3A depicts the HRP-catalyzed oxidation reaction of the fluorescent S7 to non-fluorescent hydroxylated S7 derivative.

To elucidate the structure of the product of the enzymatic oxidation of S7 by HRP in the presence of hydrogen peroxide, the $^1H$ NMR and the $^1H$-$^1H$ 2D COSY spectra of S7 before and after the reaction were compared (data not shown). After the reaction, the protons showed a change in chemical shift from 6.0 to 6.5 ppm without splitting of the peak in the $^1H$ NMR spectrum, pointing to the proposed oxidation in the six-membered ring which disrupts the $\pi$ conjugation and abolishes the near-infrared fluorescence properties. These spectra indicate that the dye S7 (the oxidized substrate in this Example) is oxidized by the peroxidase in the presence of hydrogen peroxide (see substrate and putative product of enzymatic oxidation of S7 in FIG. 3A).

Figure 3B:
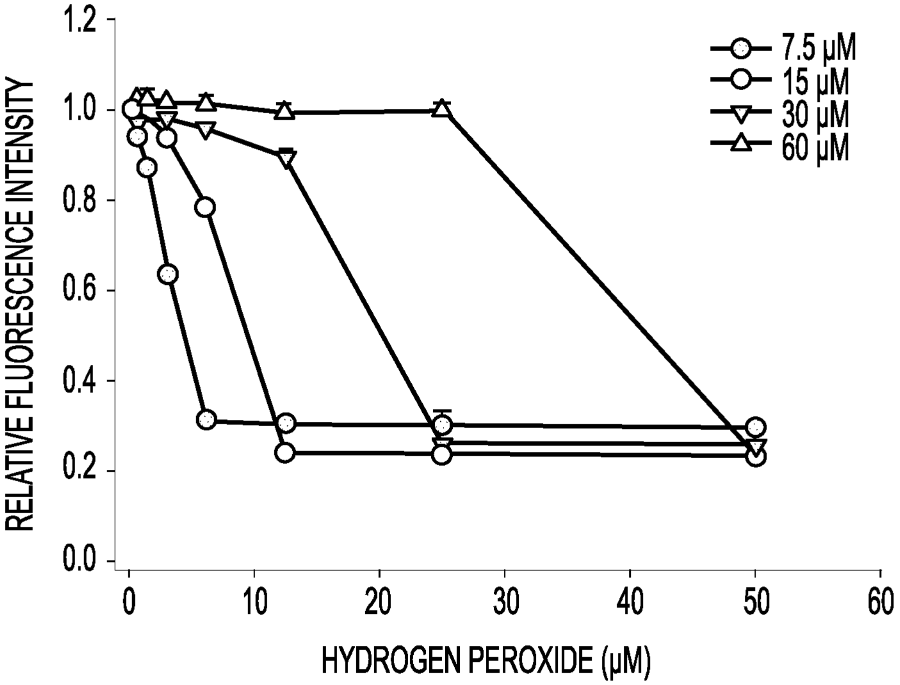
FIGS. 3B-3E are related to hydrogen peroxide sensing using HRP-mediated S7 oxidation. NIR dye concentration unless stated: 10 μM (FIG. 3C), 7.5 μM (FIG. 3D); HRP concentration: 105 mU/mL (FIG. 3B); buffer composition: phosphate buffer 50 mM at pH 7.5; 10 (FIGS. 3B, 3D) or 30 min (FIG. 3E) incubation time at room temperature. S5: sulfo-cyanine 5; S7: sulfo-cyanine 7; ICG: indocyanine green; DHE: dihydroethidium. All results as means+SD (n=3).
Figure 3C:
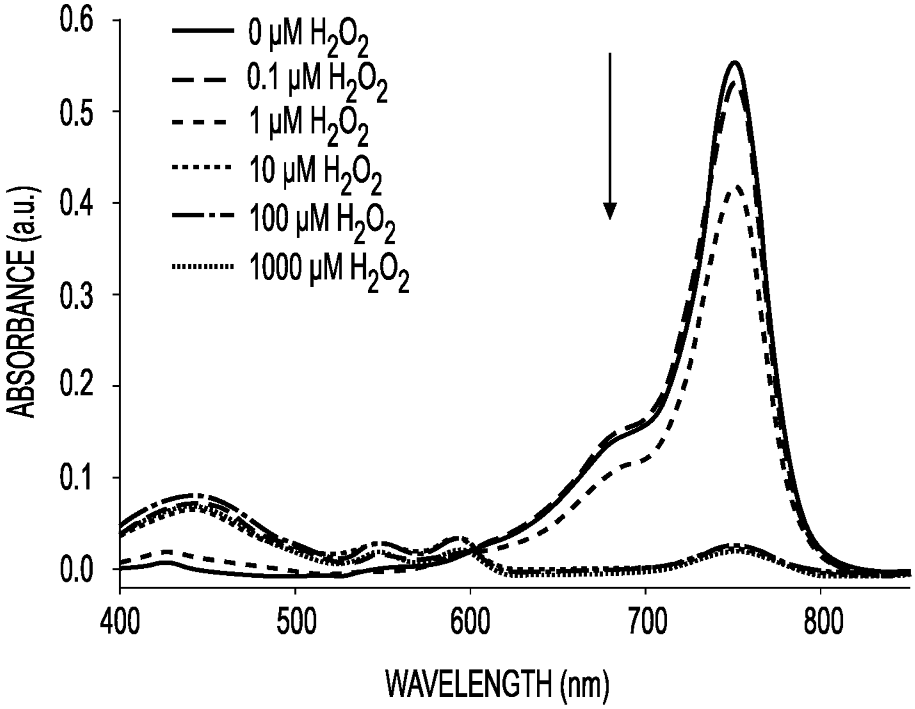
Figure 3D:
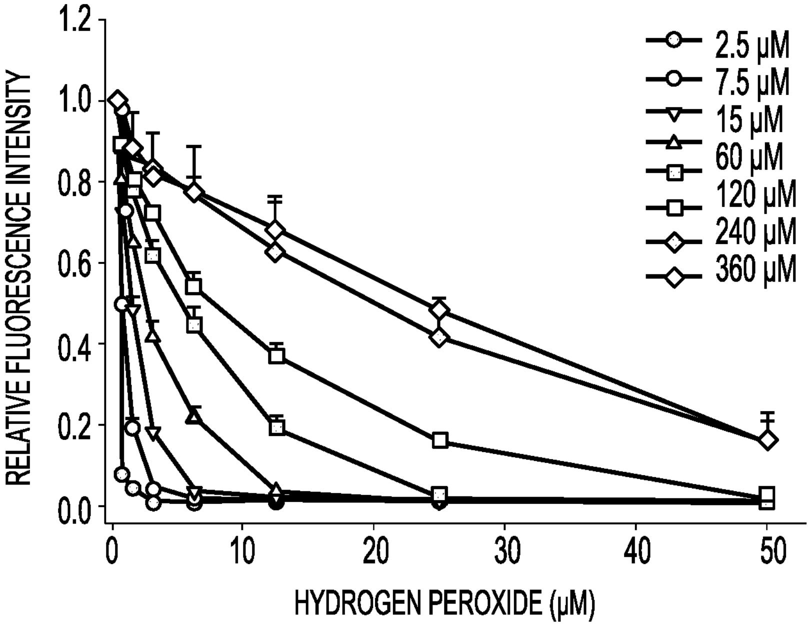
Figure 3E:
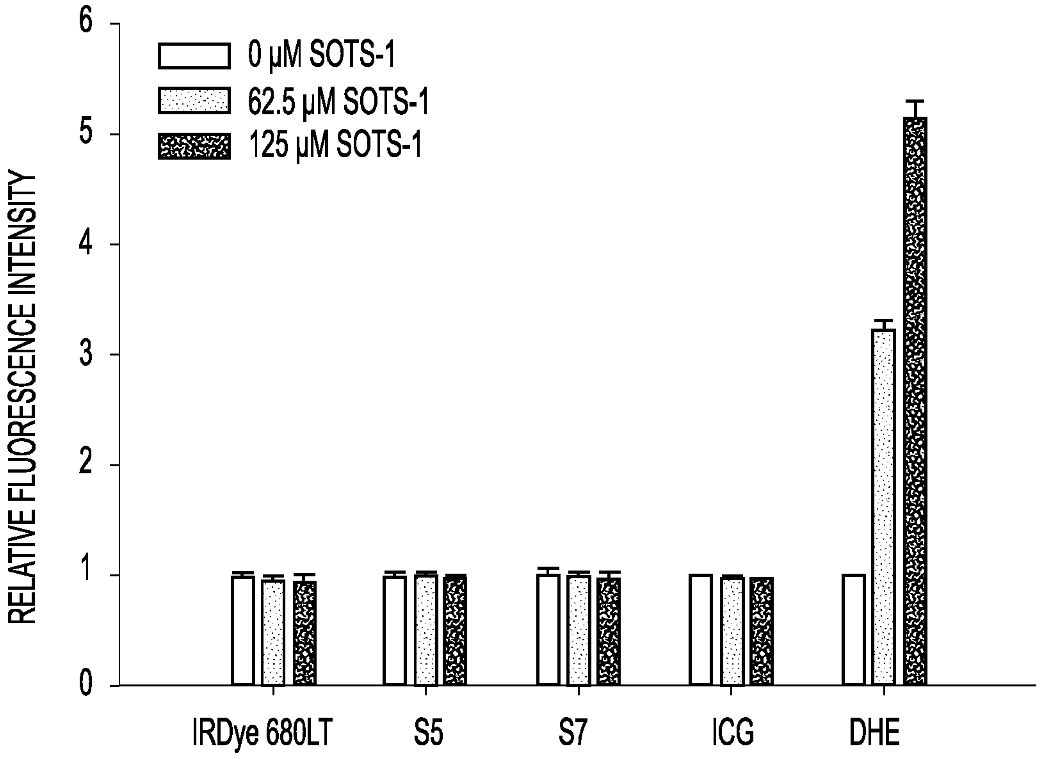
Figure 3F:
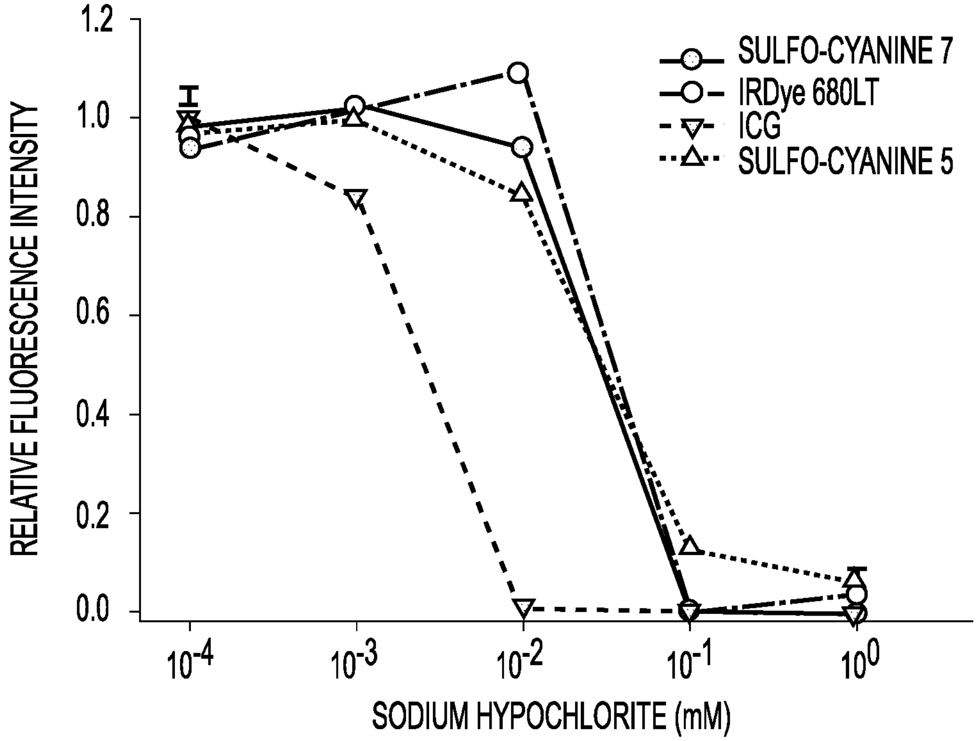
FIG. 3F is a graph showing the relative fluorescence intensity of different NIR dyes at different sodium hypochlorite concentrations.

To characterize the hydrogen peroxide sensing properties of the S7/HRP system further, the dye concentration dependence was investigated. The loss in relative fluorescence intensity of S7 followed a sigmoid curve, providing the opportunity to sense the analyte in a binary manner (see FIGS. 3B and 3C). As the inflection point was related to the dye concentration, the hydrogen peroxide sensitivity of this assay can be modulated by adjusting the S7 concentration. Interestingly, ICG showed a linear hydrogen peroxide sensing profile (see FIG. 3D). As S7- or ICG-based near-infrared fluorescence-based hydrogen peroxide assay may be of interest in quantifying hydrogen peroxide in cell assays or biological fluids, their stability was determined in the presence of two other ROS. S7, sulfo-cyanine 5, and IRDye 680LT preserved their fluorescence emission in the presence of a 100-fold excess of the superoxide radical (see FIG. 3E), a degradation product of SOTS-1. However, all investigated dyes were degraded by another ROS, hypochlorite, a bactericidal molecule secreted by immune cells (FIG. 3F).

Example 3. Lactate Sensing

With the HRP/S7 hydrogen peroxide assay at hand, a whole blood lactate sensor based on the hydrogen peroxide-generating enzymatic oxidation of lactate was developed. As hydrogen peroxide is rapidly detoxified by the highly efficient catalase- and glutathione peroxidase-based system in erythrocytes (see FIG. 4A), all components of the lactate sensing system (lactate oxidase, HRP, S7) were encapsulated in a liposomal reaction compartment in order to protect the oxidase-generated hydrogen peroxide from detoxification (see FIG. 4B).

The selected PEGylated liposomes were composed of a high molar fraction of cholesterol and a phospholipid with a relatively high phase transition temperature (1,2-dipalmitoyl-sn-glycero-3-phosphocholine, DPPC, $T_m$=41° C.), an established liposomal formulation with high stability and low permeability. While a high permeability would accelerate the diffusion kinetics of the analyte across the hydrophobic membrane, a liposome composition with low permeability was chosen to minimize dye leakage and optimize colloidal stability. The liposomes prepared in this study showed a monomodal size distribution (see FIG. 4J) with a mean hydrodynamic diameter of 7.6±0.5 μm (see Table 1), and were thus similar to non-extruded liposomes of comparable compositions.

TABLE 1

Diameter (means ± SD, n = 3) of purified liposomes by laser diffraction.

| | D10 (μm) | D50 (μm) | D90 (μm) |
|---|---|---|---|
| Liposomes | 4.5 ± 0.3 | 7.6 ± 0.5 | 12.5 ± 1.1 |

Figure 4A:
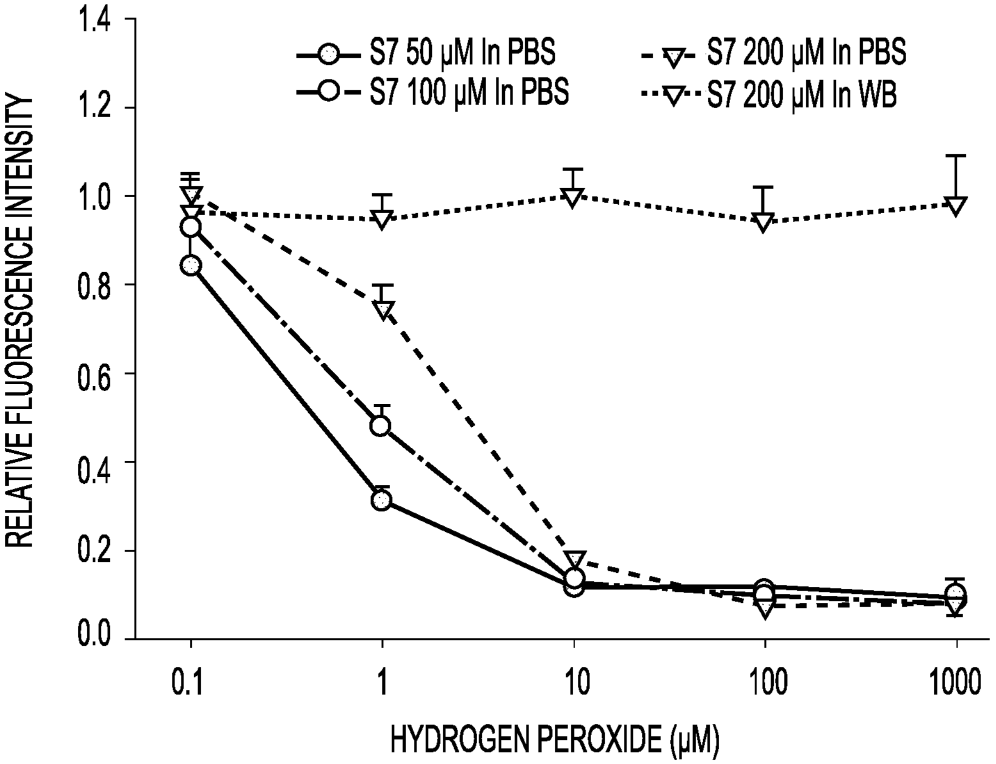
FIGS. 4A-4G are related to hydrogen peroxide and lactate sensing in PBS and lactate-spiked bovine whole blood. S7 concentration: 200 μM (C), 100 μM (FIGS. 4A, 4D, 4E, 4F); HRP concentration: 0.5 U/mL; LO concentration: 5 U/mL; buffer composition of inner phase: isotonic phosphate buffer 50 mM at pH 7.4; buffer composition of outer phase: isotonic phosphate buffer 38 mM at pH 7.4 (FIGS. 4A, 4C, 4D) or isotonic phosphate buffer 113 mM at pH 6.1 (FIGS. 4D, 4E, 4F); whole blood volume fraction: 25% (v/v) (FIGS. 4A, 4D, 4E, 4F); 10 min incubation time (unless stated otherwise) at room temperature. HRP: horseradish peroxidase, L-: lactate, LH: lactic acid, LO: lactate oxidase, P: pyruvate; S7: sulfocyanine 7, S7-OH: hydroxylated S7. The analyte concentrations (x-axis) refer to their final concentrations in the assay mixture. All results as means+SD (n=3).
Figure 4B:
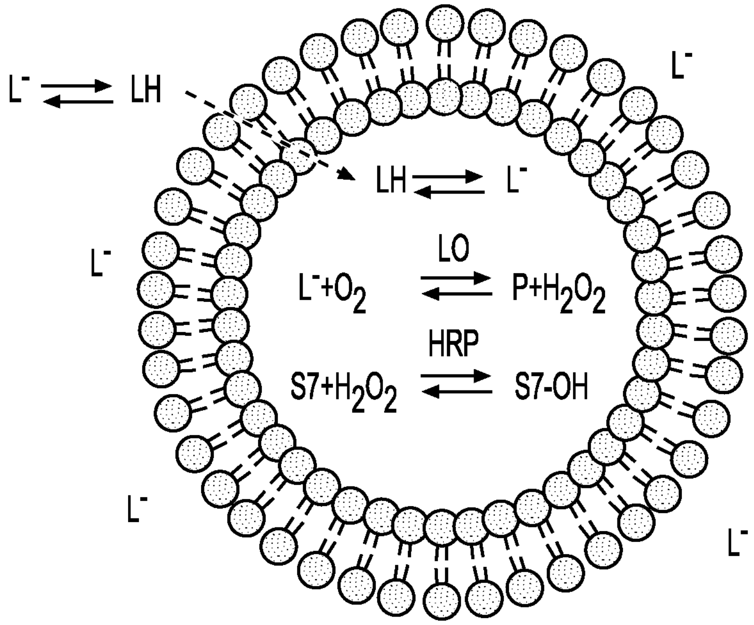
Figure 4C:
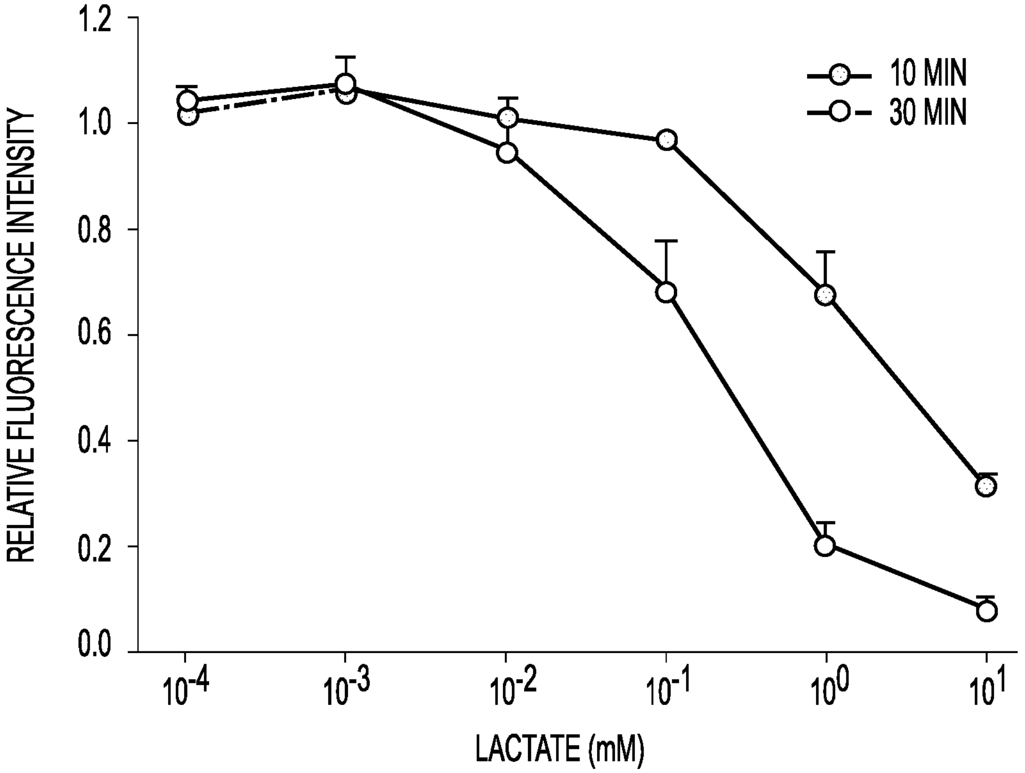
Figure 4D:
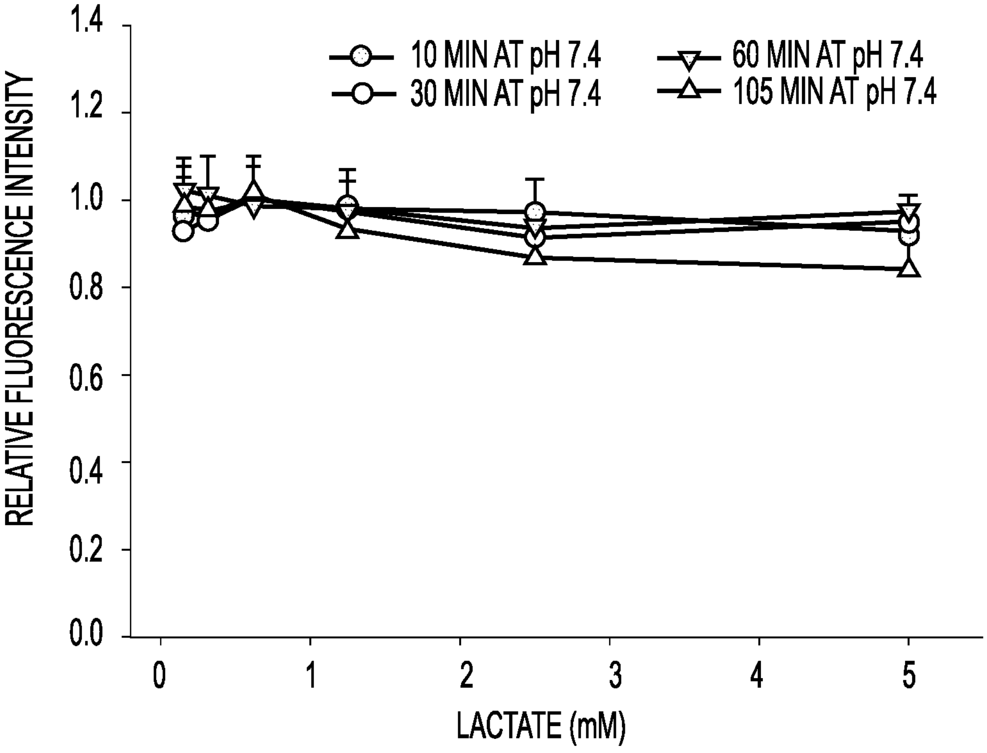
Figure 4E:
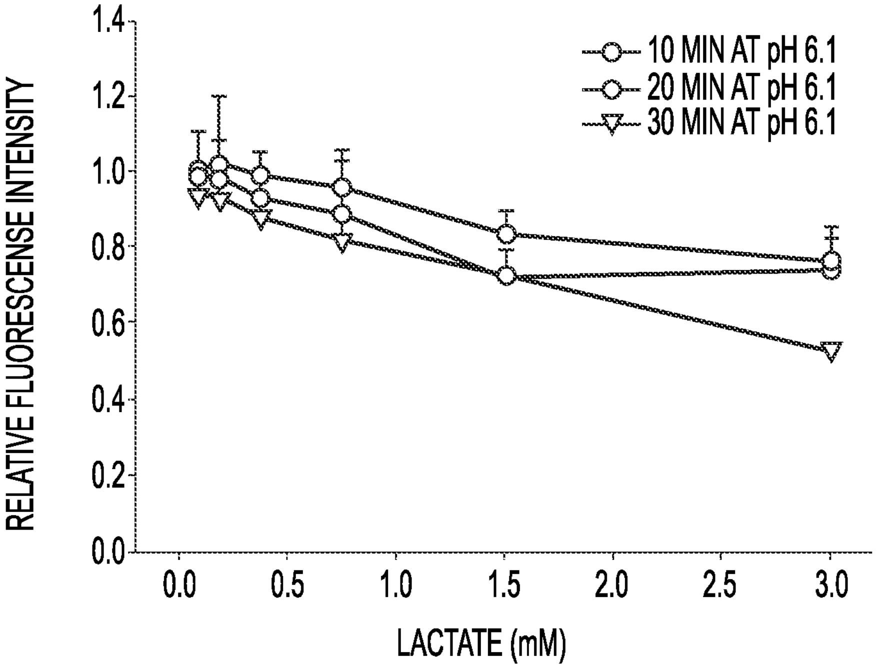
Figure 4F:
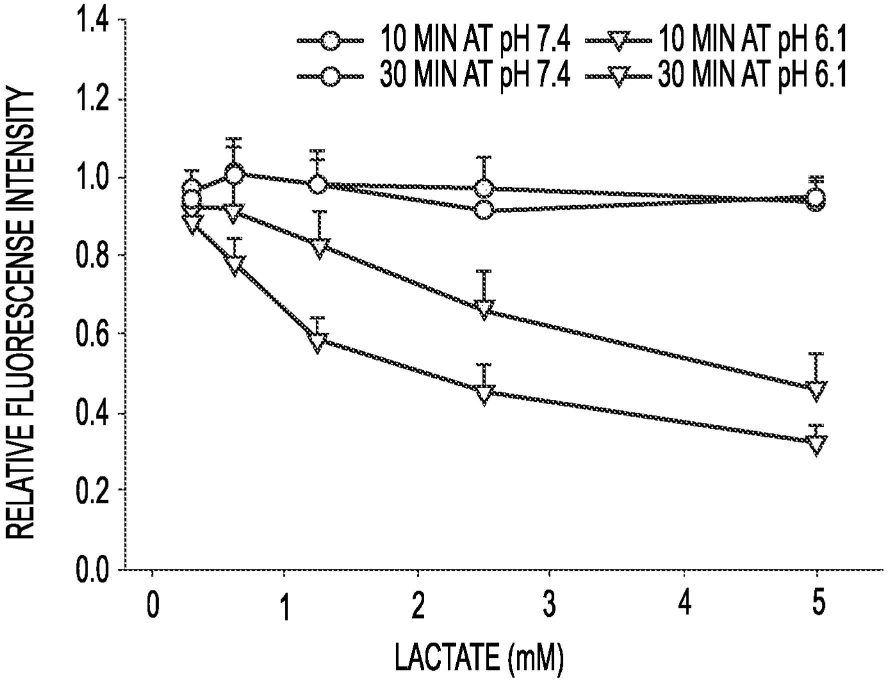

HRP/S7-containing liposomes sensed hydrogen peroxide in a dye-concentration dependent manner in isotonic PBS at pH 7.4 but did not sense this analyte in hydrogen peroxide-spiked whole blood, indicating detoxification of the analyte by erythrocytes and highlighting the need to encapsulate both the oxidase and the peroxidase in the liposomal core (see FIG. 4A). Co-encapsulating lactate oxidase with the HRP/S7 hydrogen peroxide sensing system yielded a lactate assay in the same buffer (see FIG. 4B). However, this assay showed a low response to lactate-spiked bovine whole blood at pH 7.4 over 105 min (see FIGS. 4C and 4D). After 105 min, the pH of the whole blood/PBS mixture was lowered to 6.1 and a dose-dependent response to lactate was observed after ten minutes (see FIG. 4E). Lowering the blood pH increases the fraction of lactic acid, which diffuses more rapidly across the hydrophobic liposomal membrane than the negatively charged lactate. Indeed, setting the whole blood-containing outer phase to pH 6.1 yielded a stronger fluorescence loss than at pH 7.4 after 10 min incubation (see FIG. 4F). Modifying the encapsulated dye concentration influenced the linearity and extent of the relative fluorescence decrease in the pathophysiologically relevant lactate concentration range, and 100 μM was selected as the optimal dye concentration (see FIG. 4G and Table 2). Decreasing the liposome concentration did not change the sensing properties, potentially due to the saturation of one of the involved enzymes (see FIG. 4H).

TABLE 2

Figure 4G:
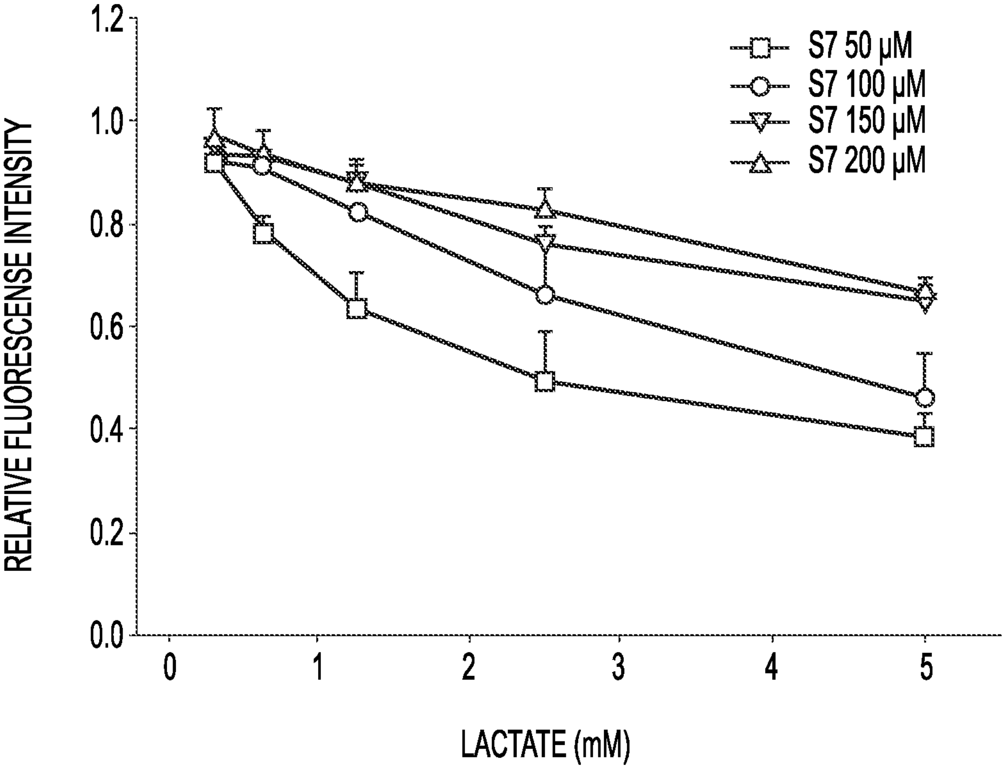
Figure 4H:
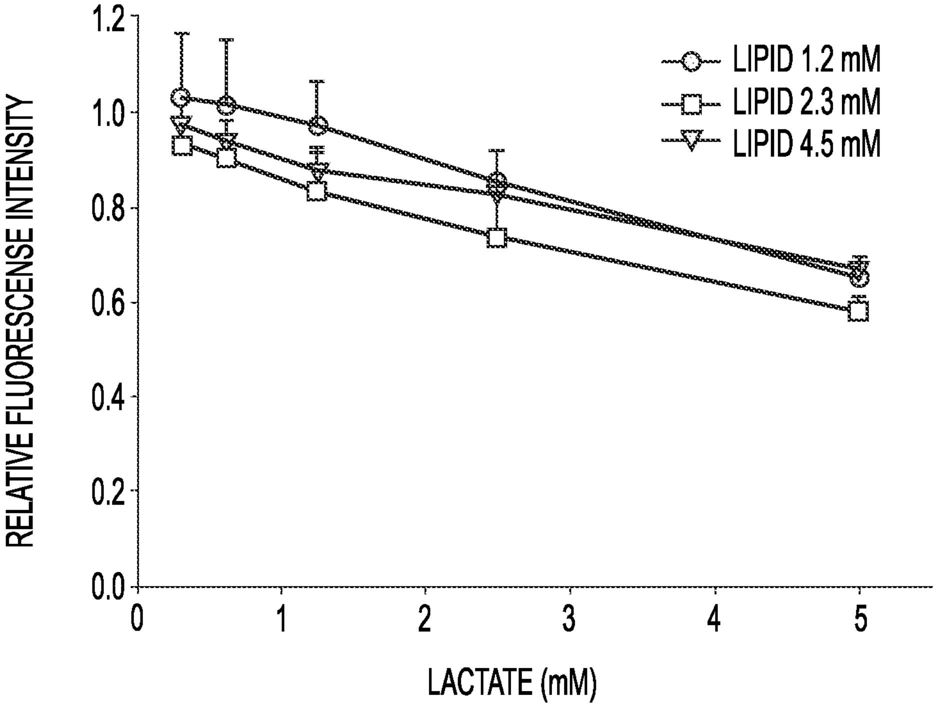
FIG. 4H is a graph showing the relative fluorescence intensity of a solution of LO/HRP/S7-containing liposomes in lactate-spiked whole blood, which evaluates the effect of lipid concentration on lactate sensing in whole blood. S7 concentration: 200 μM; HRP concentration: 0.5 U/mL; LO concentration: 5 U/mL; buffer composition of inner phase: isotonic phosphate buffer 50 mM at pH 7.4; buffer composition of outer phase: isotonic phosphate buffer 113 mM at pH 6.1; whole blood volume fraction: 25% (v/v); incubation for 10 min at room temperature. LO: lactate oxidase. All results as means±SD (n=3).
Figure 4I:
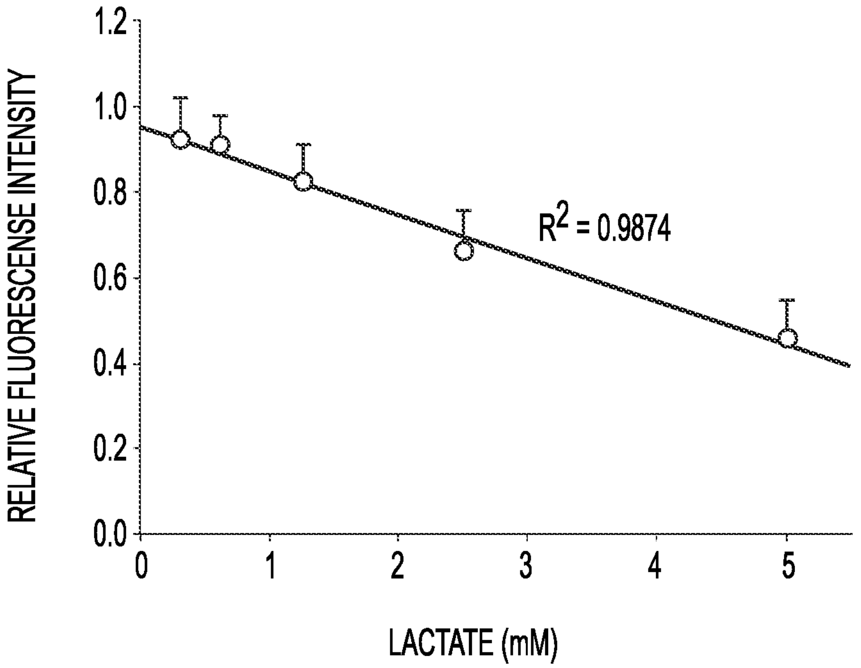
FIG. 4I is a graph showing the relative fluorescence intensity of LO/HRP/S7-containing liposomes in lactate-spiked whole blood at pH 6.1 with linear regression curve.
Figure 4J:
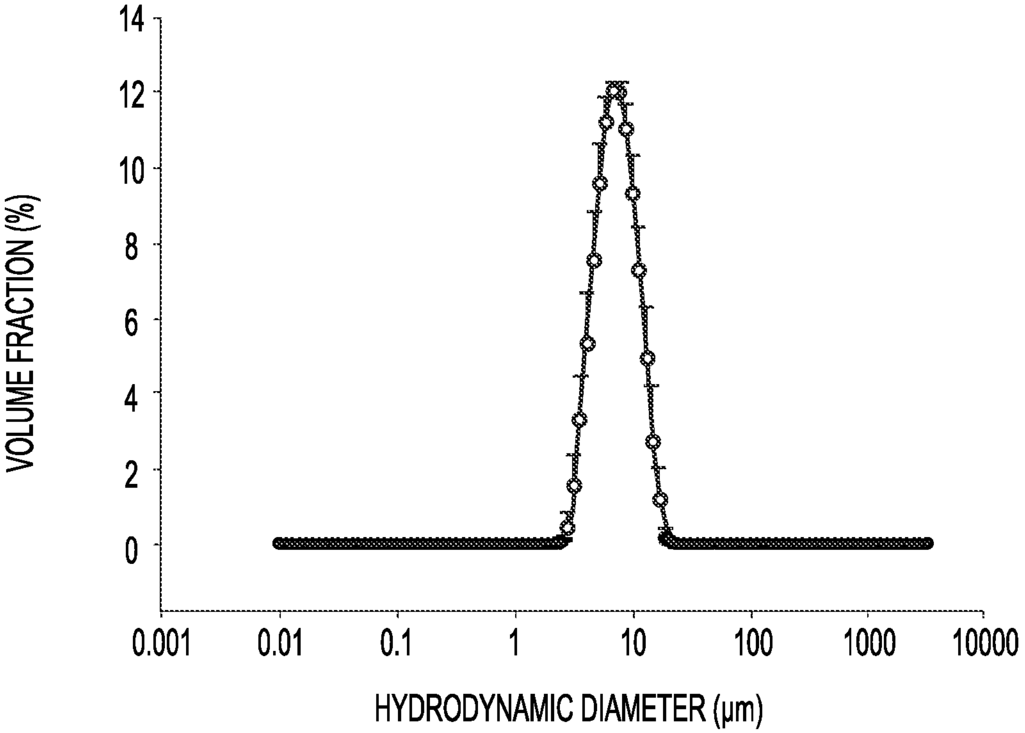
FIG. 4J is a graph showing volume distribution of PEGylated DPPC/cholesterol liposomes after purification. Results as mean±SD (n=3).

Coefficient of determination ($R^2$) and slope of linear regression curves fitted to FIG. 4G (n = 3-5).

| S7 concentration (μM) | $R^2$ | Slope |
|---|---|---|
| 50 | 0.8385 | −0.1033 |
| 100 | 0.9874 | −0.1019 |
| 150 | 0.9756 | −0.0636 |
| 200 | 0.9870 | −0.0621 |

After optimization, LO/HRP/S7-encapsulating liposomes sensed lactate in bovine whole blood in the pathophysiologically relevant range of 0.3 to 5 mM (i.e., final lactate concentration in assay mixture) after 10 min at room temperature with high linearity ($R^2$=0.9874, see FIG. 3F). Both reported lactate cut-offs in whole blood (2 or 4 mM, final concentration 0.5 and 1 mM with a blood volume fraction of 204 25%, v/v) are therefore in the linear range of our lactate assay. The fluorescence-based blood lactate assay developed in this study therefore promises to yield a rapid response in a clinically relevant range, potentially enabling bedside lactate testing and shortening the median time delay of three hours between triage and blood lactate result with the current gold standard, clinical laboratory analyzers, in hypovolemic patients. Moreover, the fluorescence-based lactate assay could further be used for the sensing of sweat lactate, an important surrogate marker for performance in sports medicine.

Example 4. Glucose, Ethanol, Methanol, and Uric Acid Sensing

Figure 5:
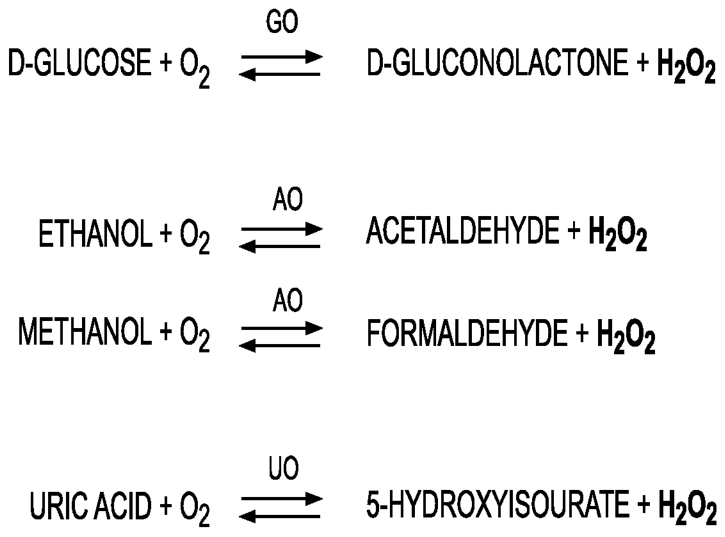
FIG. 5 sets forth the enzymatic oxidation of D-glucose, ethanol, methanol, and uric acid that each yields hydrogen peroxide.

In analogy to the lactate sensing system, the hydrogen peroxide-generating enzymatic oxidation of other metabolites (glucose, ethanol, urate) was exploited to expand the analyte spectrum of the metabolite-biosensing system developed in this study. These metabolites are generally quantified in routine clinical practice to diagnose diseases and to assess the response to therapeutic interventions. A rapid and easy-to-handle fluorescence-based assay promises to facilitate the quantification of these metabolites and to shorten the time between triage and test result both in the in- and the out-patient-setting. As the diffusion kinetics of the analyte across the liposomal membrane was an important parameter in lactate sensing, the small biorelevant molecules glucose, ethanol, and urate were investigated as metabolites of interest (see FIG. 5). Larger molecules such as cholesterol and bilirubin can potentially also be assessed by the platform described in the present disclosure if more permeable liposome formulations are employed. To reduce the dye leakage in such liposomes, S7 could be covalently conjugated to a large hydrophilic polymer (e.g., poly(ethylene glycol), dextran) with the risk of reducing the affinity of HRP to the dye.

Glucose Sensing

Figure 6A:
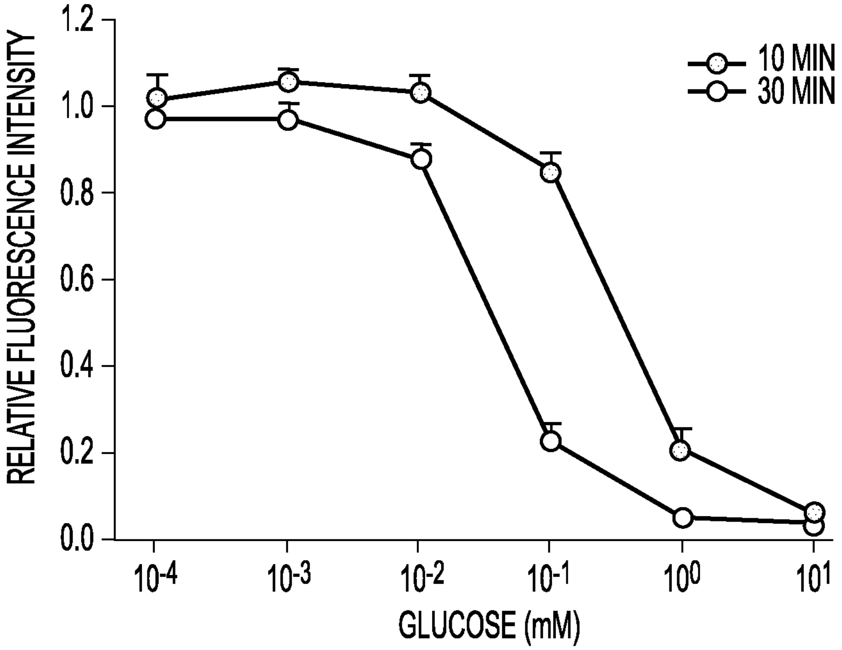
FIGS. 6A-6C evaluate glucose sensing in PBS and in glucose-spiked bovine whole blood.
Figure 6B:
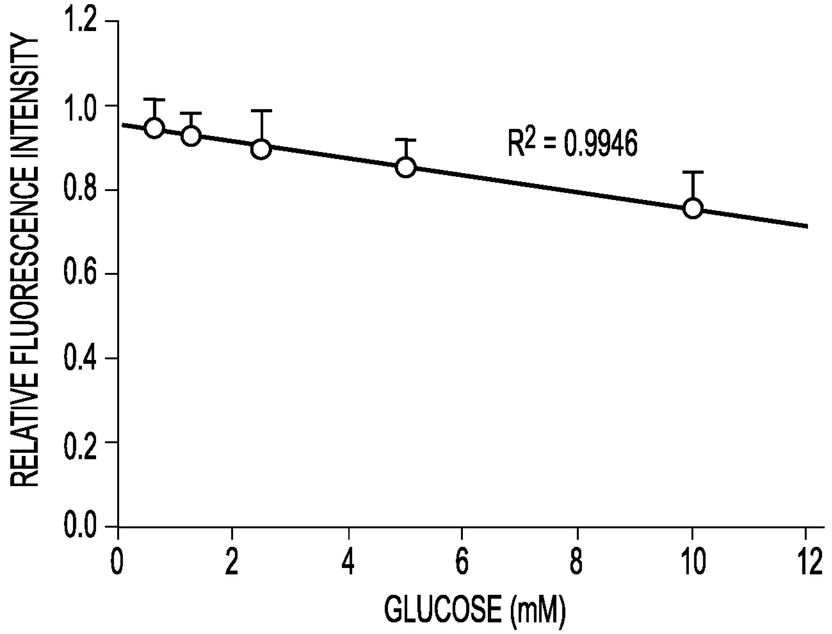
Figure 6C:
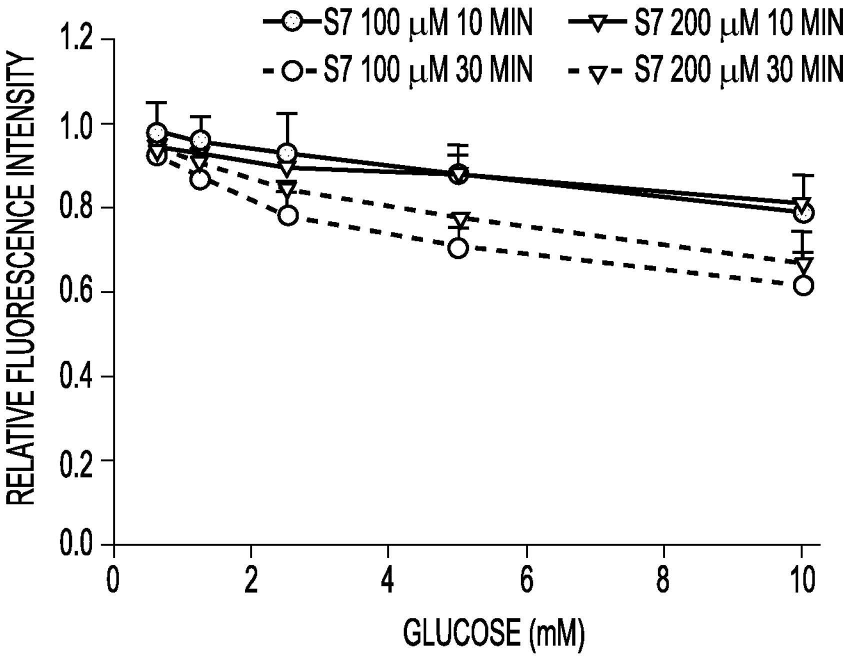

Encapsulating glucose oxidase (GO) in HRP/S7-containing liposomes yielded a glucose concentration-dependent decrease in fluorescence emission in the low millimolar range after ten minutes (see FIG. 6A). In whole blood, the GO/HRP/S7-containing liposomes sensed glucose in a linear fashion in a pathophysiologically relevant range after ten minutes ($R^2$=0.9946, see FIG. 6B). The established blood glucose cut-off of 7 mM was in the linear range of the assay. Changing the dye concentration did not alter the extent of fluorescence loss (see FIG. 6C), pointing to enzymatic or diffusion-related rate-limiting steps.

Ethanol and Methanol Sensing

Figure 7A:
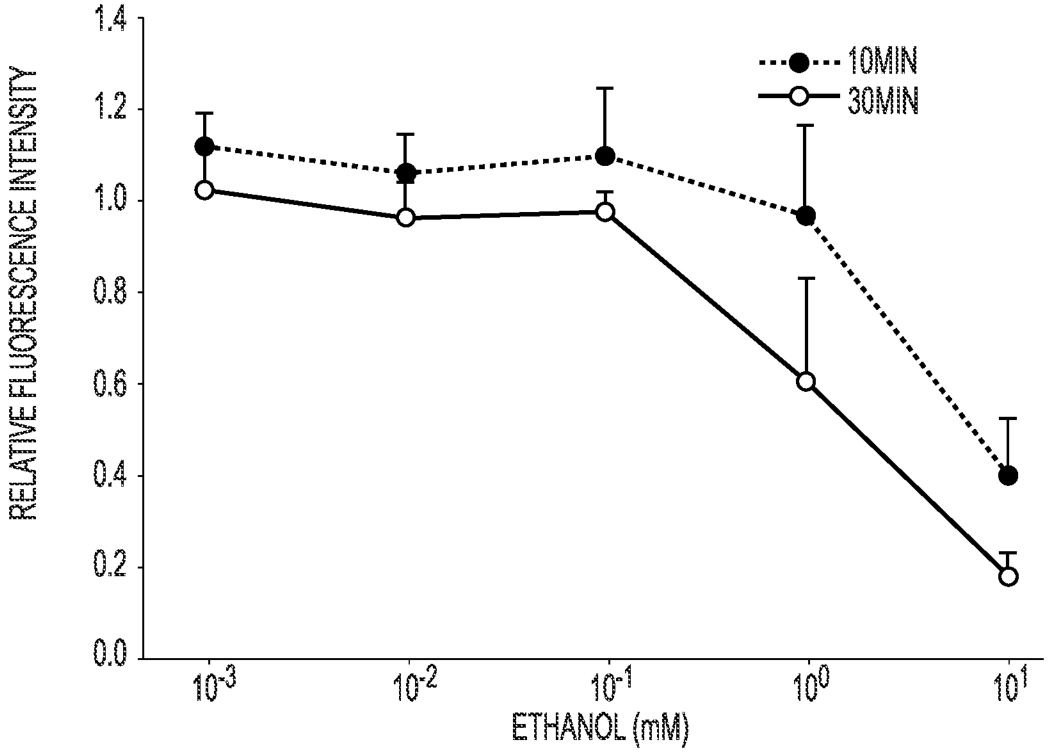
FIGS. 7A-7E evaluate alcohol sensing in PBS and in ethanol- or methanol-spiked bovine whole blood.
Figure 7B:
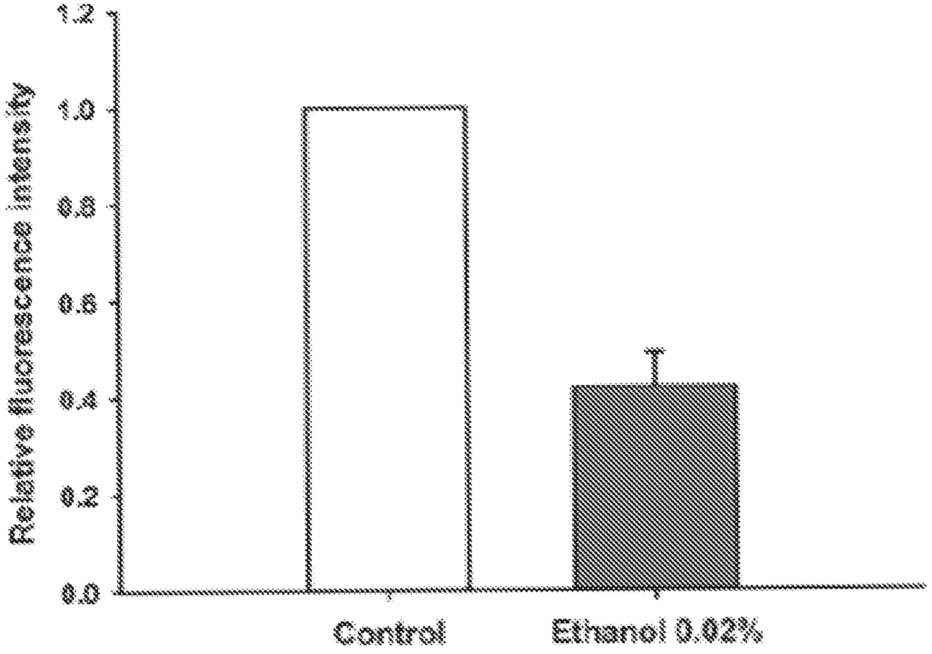
Figure 7C:
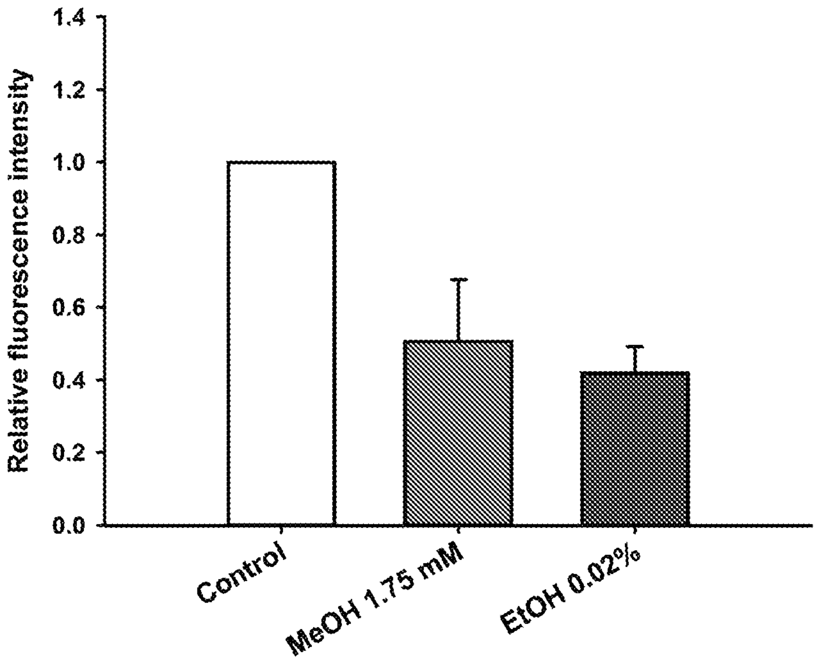
Figure 7D:
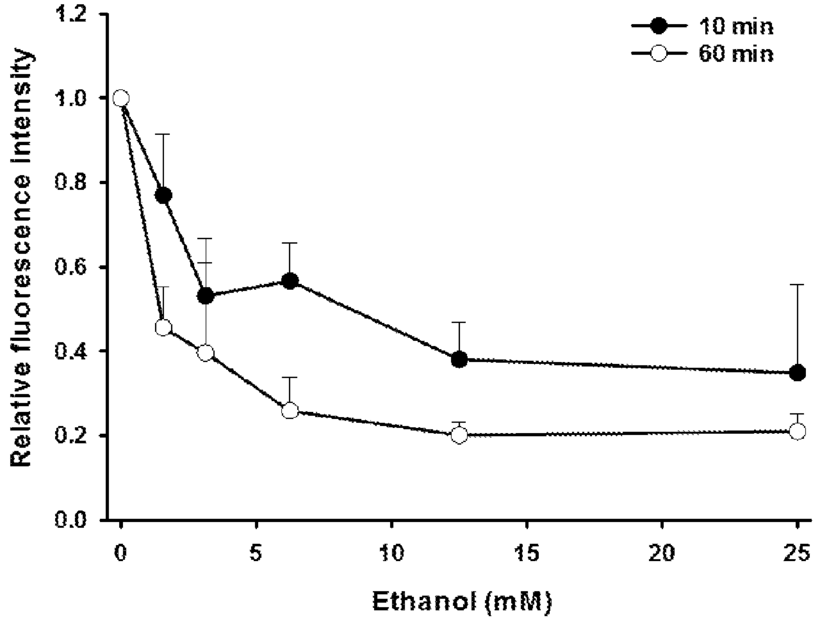
Figure 7E:
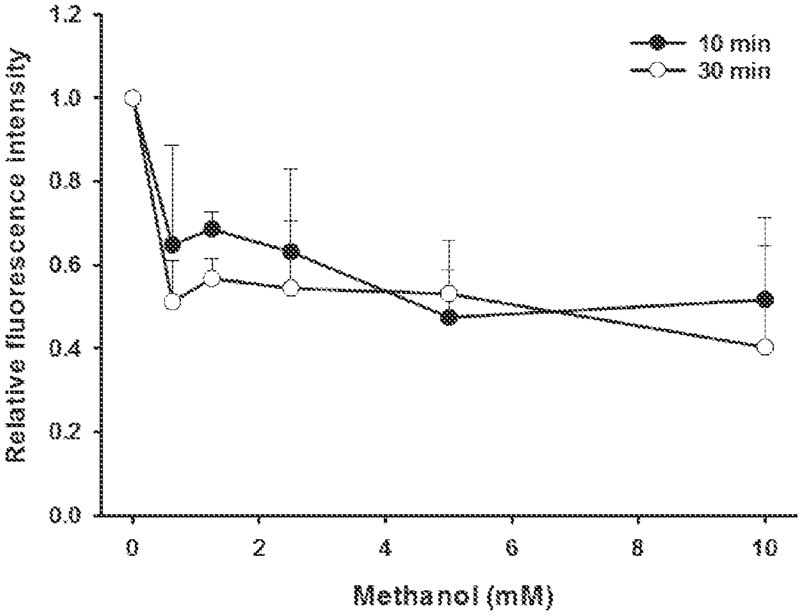

To enable ethanol sensing with the fluorescent assay described in the present disclosure, alcohol oxidase (AO) was co-encapsulated with HRP and S7 in liposomes, yielding an ethanol concentration-dependent decrease in fluorescence emission after ten minutes at pH 7.4 (see FIG. 7A). AO/HRP/S7-containing liposomes were capable of discriminating a whole blood sample spiked with an ethanol concentration of 0.08% (final 0.02%, whole blood volume fraction 25%, v/v) from a non-spiked control (see FIG. 7B). This concentration corresponds to the blood alcohol cut-off in Massachusetts. Furthermore, the ethanol- and methanol-sensing liposomes showed a response to elevated blood ethanol/methanol levels typically seen in acute methanol intoxications in spiked bovine whole blood (see FIGS. 7C and 7D). Therefore, the developed fluorescence-based metabolite assays show promise both for out-patient (routine glucose measurements, assessment of fitness to drive) and for in-patient settings (hyperlactatemia, acute methanol intoxications).

Uric Acid Sensing

Figure 8:
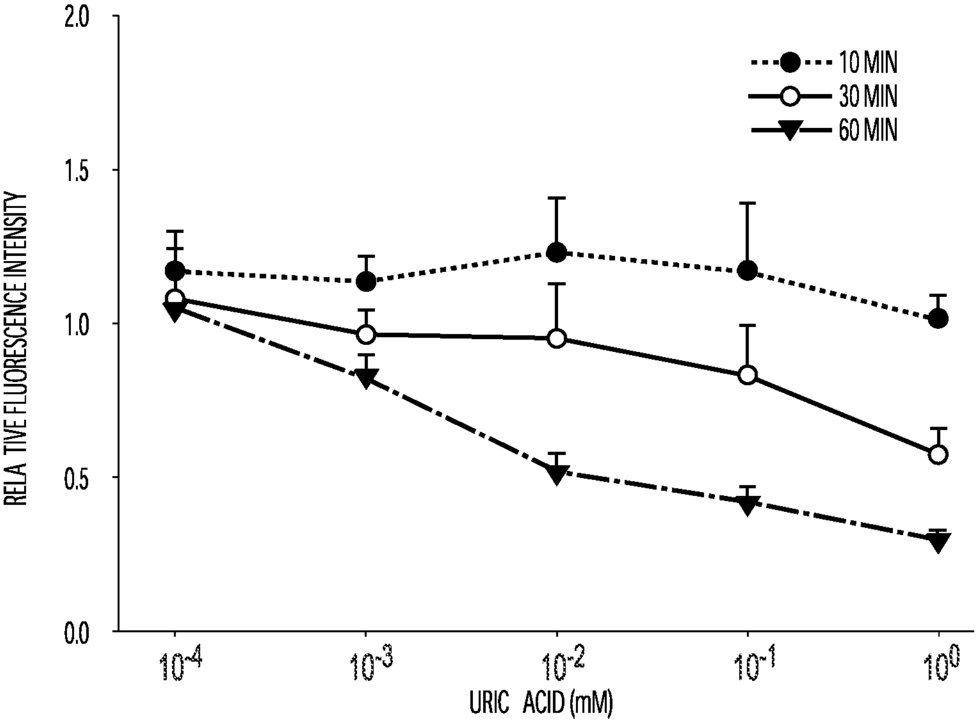
FIG. 8 evaluates uric acid sensing in PBS. Specifically.
Figures 9A, 9B, 9C, 9D, 9E, 9F:
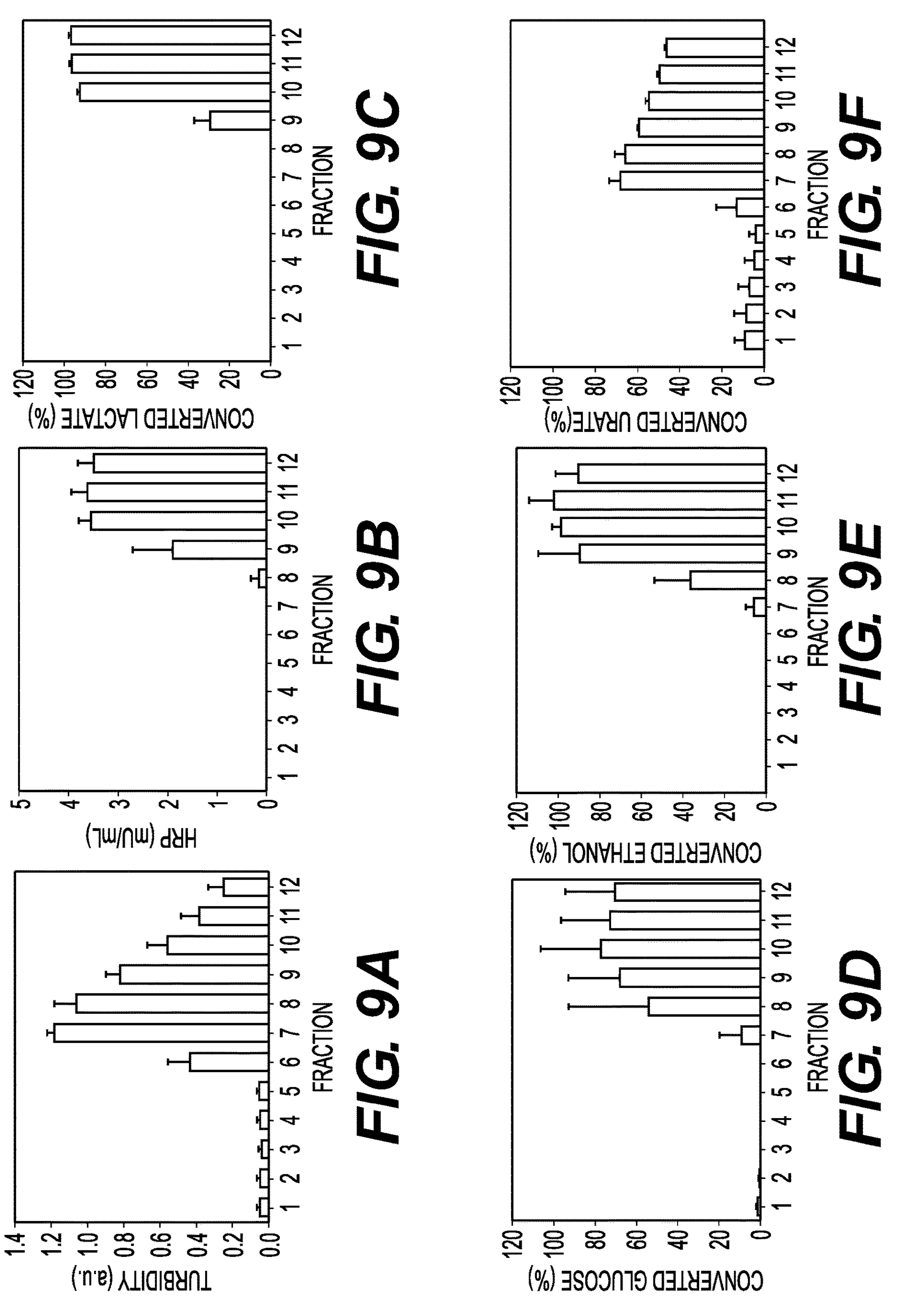
FIGS. 9A-9F evaluate the purification procedure using Sepharose® CL-6B columns.

Co-encapsulating urate oxidase with HRP with S7 in liposomes yielded a uric acid concentration-dependent decrease in fluorescence emission after 30 min in PBS at pH 7.4 (see FIG. 8).

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A composition, comprising:

an oxidase;

a peroxidase;

a chemical compound that is a substrate for the peroxidase, wherein the chemical compound is:

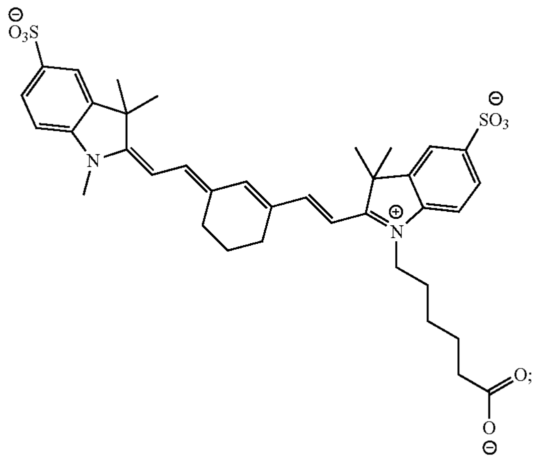

(sulfo-cyanine 7)

and a vesicle comprising a lipid or polymeric bilayer;

wherein the vesicle encapsulates the oxidase, the peroxidase, and the chemical compound.

2. The composition according to claim 1, wherein the chemical compound is selected from the group consisting of a fluorophore, a chromophore, and a luminophore; and wherein upon being acted upon by the peroxidase, the chemical compound emits a detectable signal.

3. The composition according to claim 2, wherein upon being acted on by the peroxidase, (i) the chemical compound emits a detectable signal that is the result of a loss of fluorescence or luminescence, or (ii) the chemical compound emits a detectable signal that is detectable in whole blood, or (iii) the chemical compound emits a detectable fluorescence signal that is detectable in the near-infrared (NIR) wavelength region.

4. The composition according to claim 1, wherein the chemical compound is present in the composition at a concentration of about 50 μM to about 500 μM, and/or the oxidase is present in the composition at a concentration of about 2 U/mL to about 20 U/mL, and/or the peroxidase is present in the composition at a concentration of about 0.1 U/mL to about 1.0 U/mL, and/or the vesicle is present in the composition at a phospholipid concentration of about 1.0 mM to about 10.0 mM.

5. The composition according to claim 1, wherein the oxidase is capable of oxidizing an analyte to yield hydrogen peroxide.

6. The composition according to claim 1, wherein the oxidase is selected from the group consisting of lactate oxidase, glucose oxidase, alcohol oxidase, urate oxidase, cholesterol oxidase, and bilirubin oxidase, and/or the peroxidase is horseradish peroxidase.

7. The composition according to claim 1, wherein the vesicle has a level of permeability that allows uptake of an analyte from a biological sample into the vesicle, or the vesicle is a polymersome.

8. The composition according to claim 7, wherein the biological sample is a whole blood sample, and/or wherein the vesicle has a level of permeability that allows uptake of an analyte from a biological sample into the vesicle and does not allow release of the chemical compound out of the vesicle.

9. The composition according to claim 1, wherein the vesicle comprises a lipid bilayer or the vesicle is a liposome.

10. The composition according to claim 1, wherein the lipid bilayer comprises a phospholipid.

11. The composition according to claim 10, wherein the phospholipid is a PEGylated phospholipid, or the phospholipid in the lipid bilayer is a phospholipid having a gel-to-liquid phase transition temperature of 35° C. or higher, or the lipid bilayer further comprises a non-phosphorylated lipid.

12. The composition according to claim 11, wherein the phospholipid in the lipid bilayer is a phospholipid having a gel-to-liquid phase transition temperature of 35° C. or higher and the phospholipid is selected from the group consisting of egg sphingomyelin, 1,2-dipalmitoyl-sn-glycero-3-phosphocholine (DPPC), 1,2-distearoyl-sn-glycero-3-phosphocholine, and 1,2-ditetradecanoyl-sn-glycero-3-phosphoethanolamine.

13. The composition according to claim 11, wherein the lipid bilayer further comprises a non-phosphorylated lipid and the non-phosphorylated lipid is selected from the group consisting of a fatty acid, a wax, a sterol, a monoglyceride, a diglyceride, and a triglyceride.

14. A system for the detection of an analyte in a biological sample, comprising a composition according to claim 1; and a buffer solution.

15. A kit for the detection of an analyte in a biological sample, comprising a composition according to claim 1; and a buffer solution.

* * * * *